(12) United States Patent
Marggraf-Rogalla et al.

(10) Patent No.: US 11,174,508 B2
(45) Date of Patent: Nov. 16, 2021

(54) METHOD FOR DETECTING CHROMOSOMAL ABNORMALITIES

(71) Applicant: Zytovision GmbH, Bremerhaven (DE)

(72) Inventors: Piere Marggraf-Rogalla, Stuhr (DE); Sven Hauke, Bremen (DE)

(73) Assignee: Zytovision GmbH, Bremerhaven (DE)

( * ) Notice: Subject to any disclaimer, the term of this patent is extended or adjusted under 35 U.S.C. 154(b) by 0 days.

(21) Appl. No.: 15/737,536

(22) PCT Filed: Jun. 23, 2016

(86) PCT No.: PCT/EP2016/064631
§ 371 (c)(1),
(2) Date: Mar. 21, 2018

(87) PCT Pub. No.: WO2016/207325
PCT Pub. Date: Dec. 29, 2016

(65) Prior Publication Data
US 2018/0282795 A1 Oct. 4, 2018

(30) Foreign Application Priority Data

Jun. 23, 2015 (EP) .................................. 15001845
Jul. 13, 2015 (EP) .................................. 15002075
Jul. 24, 2015 (EP) .................................. 15002200

(51) Int. Cl.
*C12Q 1/6841* (2018.01)
*C12Q 1/6858* (2018.01)
*C12Q 1/6886* (2018.01)

(52) U.S. Cl.
CPC ......... *C12Q 1/6841* (2013.01); *C12Q 1/6858* (2013.01); *C12Q 1/6886* (2013.01); *C12Q 2565/101* (2013.01); *C12Q 2565/102* (2013.01)

(58) Field of Classification Search
CPC ............ C12Q 2600/156; C12Q 1/6816; C12Q 1/6841; C12Q 1/6886
See application file for complete search history.

(56) References Cited

U.S. PATENT DOCUMENTS 6,344,315 B1 2/2002 Gray et al.
6,576,421 B1 6/2003 Westbrook
(Continued)

FOREIGN PATENT DOCUMENTS

CN 103874769 6/2014
WO 9321345 10/1993
(Continued)

OTHER PUBLICATIONS

Gozzetti, A. et al. Seminars in Hematology 37(4):320 (Oct. 2000).*
(Continued)

*Primary Examiner* — Diana B Johannsen
(74) *Attorney, Agent, or Firm* — Hovey Williams LLP

(57) ABSTRACT

The invention relates to a method for identifying chromosomal abnormalities, particularly structural and/or numerical chromosomal abnormalities, and preferably structural chromosomal abnormalities, using in situ hybridization by detecting chromosomes and/ or DNA regions in a biological sample, preferably in one or more cell(s) and/or in one or more cell nuclei.

10 Claims, 9 Drawing Sheets

(56) References Cited

U.S. PATENT DOCUMENTS

| | | | |
|---|---|---|---|
| 7,964,345 B2* | 6/2011 | Palanisamy | C12Q 1/6841 435/6.11 |
| 2012/0141991 A1* | 6/2012 | Halling | C12Q 1/6886 435/6.11 |

FOREIGN PATENT DOCUMENTS

| | | |
|---|---|---|
| WO | 02093130 | 11/2002 |
| WO | 2005111235 | 11/2005 |

OTHER PUBLICATIONS

Slovak, M. et al. Cancer Detection and Prevention 26:171-179. (Year: 2002).*

Ventura, R.A. et al. Journal of Molecular Diagnostics 8(2):141. (Year: 2006).*

German Office Action in corresponding EP 15002200.2, dated Apr. 12, 2018 (English translation attached).

Gozzetti, et al., "Fluorescence In Situ Hybridization: Uses and Limitations", Seminars in Hermatology, 34(4), Oct. 2000, pp. 320-333.

Primo, et al., "Patterns of BCR/ABL gene rearrangements by interphase fluorescence in situ hybridization (FISH) in BCR/ABL+ leukemias: incidence and underlying genetic abnormalities", Leukemia, Jun. 2003, vol. 17, issue 6, pp. 1124-1129.

International Search Report and Written Opinion in corresponding PCT Application Serial No. PCT/EP2016/064631, dated Sep. 23, 2016 (English translation attached).

International Preliminary Report on Patentability in corresponding PCT Application Serial No. PCT/EP2016/064631, dated Jan. 4, 2018 (English translation attached).

Valm, et al., "Systems-level analysis of microbial community organization through combinatorial labeling and spectral imaging", PNAS, Mar. 8, 2011, vol. 108, issue 10, pp. 4152-4157.

Behnam, et al., "A Straightforward DOPE (Double Labeling of Oligonucleotide Probes)—FISH (Fluorescence In Situ Hybridization) Method for Simultaneous Multicolor Detection of Six Microbial Populations", Applied and Environmental Microbiology, Aug. 2012, vol. 78, issue 15, pp. 5138-5142.

* cited by examiner

Fig. 7
a) No abnormalities:
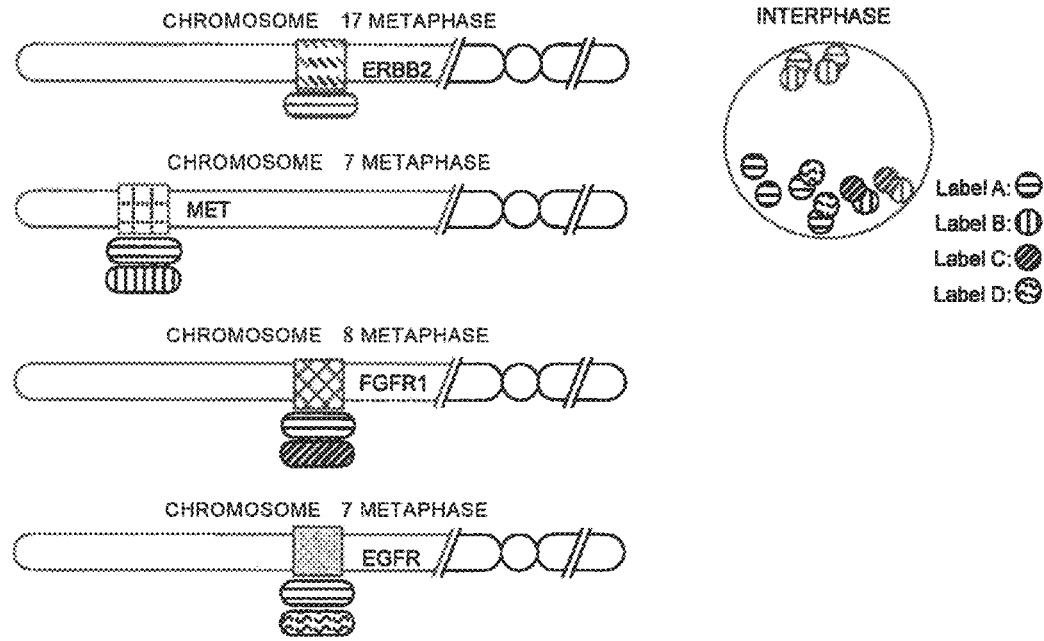
b) MET amplification:
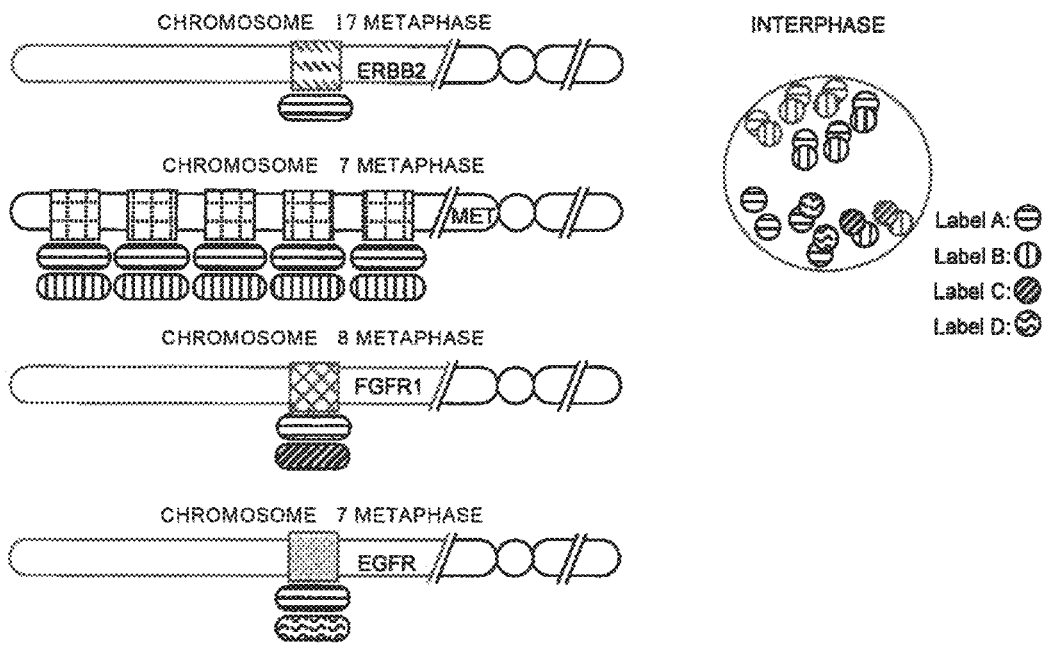

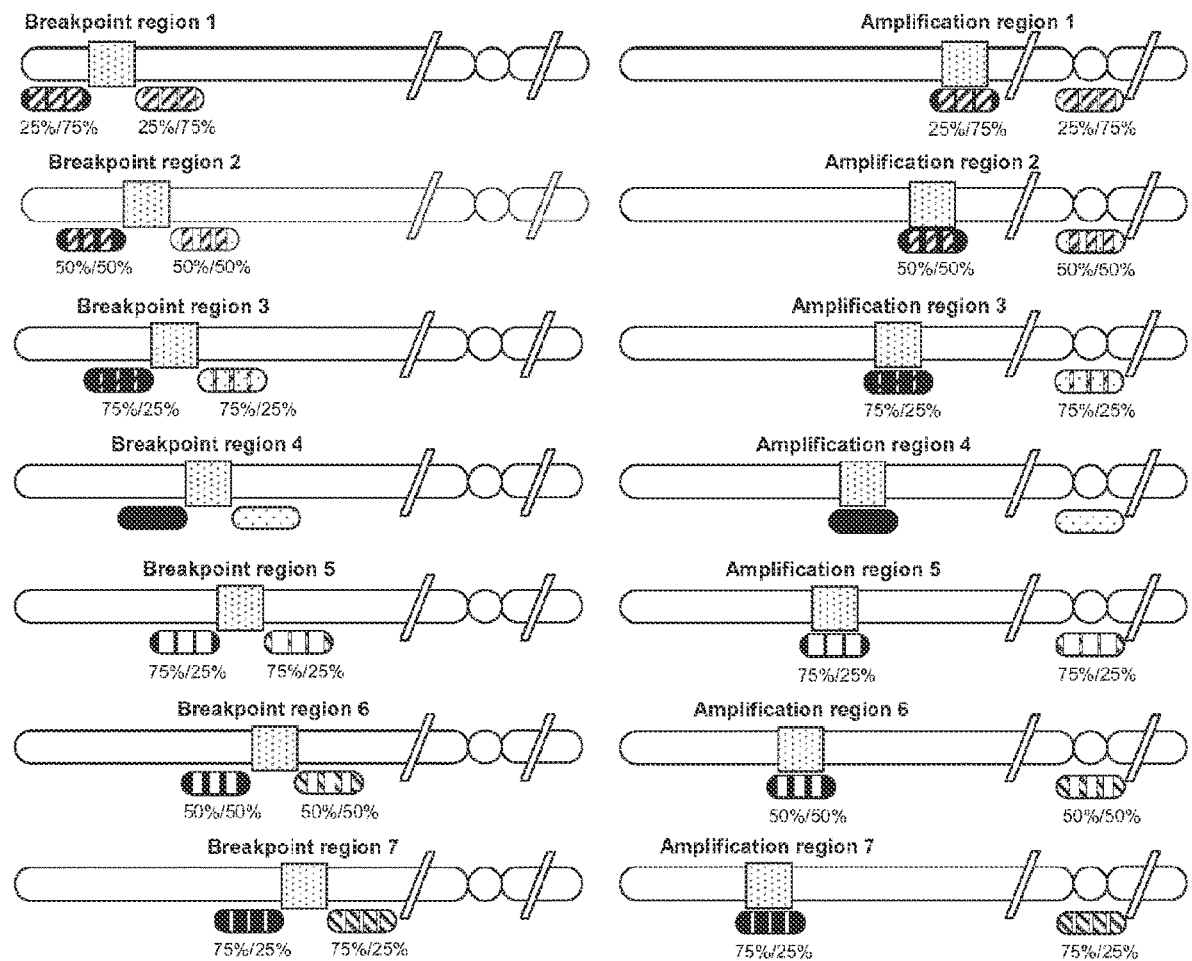
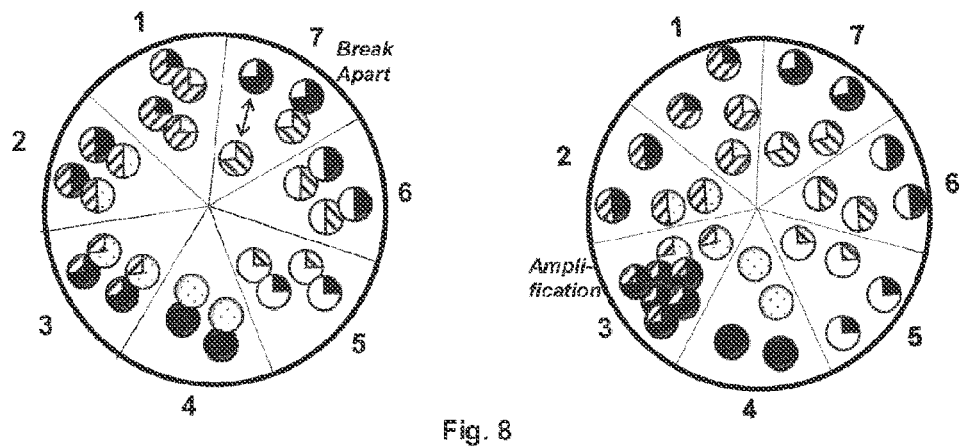
Fig. 8

METHOD FOR DETECTING CHROMOSOMAL ABNORMALITIES

RELATED APPLICATIONS

This application is the U.S. National Stage of International Patent Application No. PCT/EP2016/064631, filed Jun. 23, 2016, which is hereby incorporated by reference in its entirety, and which claims priority to European Patent Application No. 15001845.5, filed Jun. 23, 2015, European Patent Application No. 15002075.8, filed Jul. 13, 2015 and European Patent Application No. 15002200.2, filed Jul. 24, 2015.

BACKGROUND

The present invention relates to the technical field of detection methods for chromosome anomalies or chromosome abnormalities.

In particular, the present invention relates to a method for detection of chromosome abnormalities by means of in situ hybridization. Furthermore, the present invention relates to a composition suitable for detection of chromosome abnormalities, as well as its uses according to the invention. A further object of the present invention is use of locus-specific hybridization probes marked with detection labels. Finally, a kit for detection of chromosome abnormalities is an object of the present invention.

Many tumor illnesses are based on structural and numerical chromosome mutations, such as translocations, inversions, segmental duplications, deletions, insertions, duplications, aneuploidies, and amplifications. Detection of these changes as a predictive, prognostic or differential-diagnostic marker generally takes place by means of in situ hybridizations (ISH).

In situ hybridization is based on hybridization or pairing of complementary bases of nucleic acid single strands, particularly DNA single strands, so that specific nucleic acid sequences in a sample, particularly in a tissue or cell preparation, can be detected. For this purpose, synthetically produced probes, marked directly or indirectly, are hybridized with nucleic acid single strands of the sample and subsequently detected.

For detection purposes, fluorescence-marked nucleic acid fragments or fluorescence-marked hybridization probes (fluorescent ISH (FISH)) can be used. Furthermore, antigen-marked probes, particularly hapten-marked probes, can be used, which are subsequently made visible using antibodies, by means of color reactions, so that light-microscopy analysis is possible ((bright field ISH (BrISH), chromogenic ISH (CISH), silver ISH (SISH)).

The advantage of FISH is that multiple genomic regions can be detected simultaneously and so as to be distinguished from one another. For this purpose, nucleic acid fragments that address different genomic regions or are specific for them are marked or coupled with different fluorescence dyes, in each instance, which differ from one another in terms of their adsorption spectrum and/or emission spectrum. If such multi-color probes, which comprise separate, different single probes, are used on metaphase-chromosome preparations or on interphase cell nucleus preparations, the individual colors can be depicted separately from one another by means of the use of specific microscope filters, which conduct precisely defined wavelength ranges of light onto the preparation to excite the dyes, and also conduct precisely defined wavelength ranges of the light emitted by the dyes to the evaluator (called single bandpass filter set). Furthermore, filters and filter sets also exist that permit simultaneous depiction of different fluorescence dyes and thereby multiple nucleic acid fragments. In the case of two different fluorescence dyes, for example, one speaks of a dual-bandpass filter set.

However, clear limits are set for simultaneous depiction, since only one label can be used per genomic region that is detected by a specific probe. Furthermore, the absorption and emission ranges of the dyes frequently lie so close to one another that they cannot be separated from one another by the microscope filter sets. For these reasons, usually only two colors (orange/red and green) or three colors (orange/red and green simultaneously or together with a blue nucleus counter-color (DAPI)) are analyzed simultaneously in FISH. Approximately the same restrictions that can be depicted for FISH also apply to BrISH. Here, the state of the art is the use of two haptens, generally selected from the group of biotin, dinitrophenyl (DNP), and digoxigenin, and two antibody-coupled enzymes, generally alkaline phosphatase and peroxidase.

The said restrictions in simultaneous depiction or analysis have a decisive influence on the composition (composition) or coordination of the probes for detection of structural and numerical chromosome abnormalities, which can be carried out for diagnosis of tumors with cells situated in the interphase, only with what are called locus-specific probes, where occasionally, what are called repetitive sequence probes are also used for detection of numerical chromosome mutations.

Locus-specific probes are understood to be probes that address selected DNA segments of a chromosome, generally individual genes or adjacent genes, with a size of up to about 1,000 kb, in total, and are referred to as gene-specific probes or "single-copy" probes. Repetitive sequence-specific probes are probes that address repetitive sequences and therefore address regions having a size of multiple 1,000 kb. These probes also include centromere probes or alpha-satellite probes, for example.

With regard to detection of translocations and inversions, there are fundamentally two decisive techniques and underlying probe compositions or probe compositions: The principle of the occurrence of fusion signals (called Dual-Color-Dual-Fusion approaches) (WO 02/093130 A2) on the one hand, and the separation of fusion signals (called Dual-Color-Break-Apart or Dual-Color-Split approaches), on the other hand. In the following representation of these two principles and in the derived signal patterns, it must be noted that a normal cell is generally diploid, i.e. every allele is present in duplicate. Because generally only one of the two alleles is affected by abnormalities, in each instance, the normal signal of the allele not affected by the abnormality is also visible along with the abnormal signal. For a better understanding, the signal pattern of the normal signal will not always be described explicitly in the following.

In Dual-Color-Dual-Fusion approaches, the region of a first breakpoint of the chromosome is flanked, proximally and distally, by nucleic acid fragments of the same color (e.g. orange), and the region of a second breakpoint, i.e. the reciprocal translocation partner, is flanked by a second color (e.g. green) proximally and distally of nucleic acid fragments. The normal situation, i.e. without chromosomal breaks in the region of the two translocation partners, is characterized by a green and a spatially separate orange signal, in this regard.

In the case of reciprocal translocation, breaks occur within the breakpoints of both translocation partners, and the proximal region of the one translocation partner fuses with the distal region of the other partner and vice versa. Therefore two green/orange signal pairs occur, also called fusion signals, because the differently colored signals often overlap. The disadvantage of this probe technique is that the fusion signals only occur if the breakpoints of the two translocation partners lie in the region of the respective marked nucleic acid fragments. No fusion signals occur in the case of translocations that relate only to one of the two partners. In this regard, only the formation of an additional signal occurs, which has the color of the signal that is characteristic for the partner affected by the translocation. This means that an additional green signal occurs if the breakpoint of the translocation lay in the region that was covered by the nucleic acid marked with the green fluorochrome. A disadvantage of this probe composition is that only the two breakpoint regions of the same translocation or inversion are marked using the two colors used, and therefore only a specific translocation or inversion can be detected.

In the case of Dual-Color-Break-Apart approaches, the region of a breakpoint is flanked, proximally and distally, by differently marked or color-marked nucleic acid fragments (e.g. distal orange, proximal green). The normal situation, i.e. without a chromosomal break in this region, is characterized by a fusion signal, in this regard. In an abnormal situation, i.e. if a chromosomal break occurs between the probe fragments, the signals hardly separate spatially from one another. The difference between the normal situation and the abnormal situation is therefore characterized by the distance between the differently colored signals. Statements regarding participating translocation partners are not possible with this method. It merely permits the conclusion that a specific chromosomal rearrangement has taken place. A disadvantage of this probe composition is that only a single breakpoint region and therefore only one specific translocation or inversion can be detected with the two colors used.

As far as deletions, aneuploidies and amplifications are concerned, usually only one decisive technique and underlying probe composition, which generally relates to locus-specific probes, is used. Under some circumstances, however, locus-specific probes are also supplemented with what are called repetitive-sequence-specific probes, such as, for example, centromere probes or alpha-satellite probes: The principle of the detection of gain or loss of signals resulting from the occurrence of deletions, aneuploidies, and amplifications usually takes place with what are called Dual-Color-Probe approaches. In this principle, as well, which will be described below, and the signal patterns derived from it, it must be noted that a normal cell is generally diploid, i.e. every allele is present in duplicate.

In Dual-Color-Probe approaches, two different chromosomal regions are marked with differently marked or color-marked nucleic acid fragments (e.g. genomic region 1 or target region 1 in orange, genomic region 2 or target region 2 in green). The normal situation, i.e. without gain or loss of these regions, is characterized by two orange and two green signals. In an abnormal situation, i.e. when a gain or loss of genomic regions in the target regions 1 and/or 2 has occurred, fewer green and/or orange signals are visible in the case of a loss, more signals in the case of a gain. In the case of strong gene amplifications or amplifications of genomic regions, many additional signals can be visible, which can also be depicted as clusters.

With the aforementioned standard methods and standard compositions, and using two standard signals or two standard colors, only one (possible) abnormality can therefore be detected in the case of structural changes, and maximally two (possible) abnormalities per method can be detected in the case of numerical chromosome mutations, per method.

Aside from the two two-color applications listed above, three-color, rarely four-color, and very rarely five-color probes are also used in FISH analyses. By definition, methods that simultaneously use at least three different ligands or fluorochromes—without the counter-coloring—for marking the probes are Multicolor-FISH methods (mFISH methods). In this regard, not only the clearly stronger standard fluorescence colors orange/red and green, but also the further available weaker colors, e.g. gold or gold/yellow or gold-colored, red or blue are used. For this reason, in general, four-color FISH probes, for example, are used only for detection of deletions or amplifications, because here, it is generally possible to fall back on repetitive sequences for amplification of the color intensities of blue and gold, for example, in the case of the markings of the probes. Such methods are described in EP 1 035 215 B1, WO 2007/028031 A1, and EP 0 549 70961, among others.

Furthermore, in the state of the art, triple FISH approaches are described, which address the detection of different translocation events, which can cluster next to one another in a chromosomal region (i.e. different genes are involved, which are located near one another). In this regard, only two colors are analyzed, in each instance, for the corresponding evaluation of the signal patterns, which detect a single abnormality, with the third color not playing a role, in each instance. Three different locus-specific probes are used, which are marked with a different label, in each instance.

As far as bright-field (BrISH) using more than two colors is concerned, in the state of the art in this regard, carrying out chromogenic triple in situ hybridization is described, which is aimed, in general, at detection of three repetitive chromosomal regions. According to the current state of the art, translocations are detected by means of BrISH only when using two haptens and therefore two dyes. In the patent application WO 2012/150022 A1, a method is described that discloses the use of three different probes by means of the BrISH method, using the three labels biotin, digoxigenin, and DNP, which lead to three different colors, for detection of inversions.

WO 2005/111235 A2 describes a method that comprises the use of three colors for detection purposes. However, the chromosomal region that is marked by the third label of a probe is not directly affected by a change, so that in the case of a chromosome structure change, the first fusion signal is eliminated, so that a new split signal and a new fusion signal occur. This method uses probes that are each marked with only one label. Furthermore, with this method only one possible translocation, which is predetermined by the probes, can be detected.

WO 02/093130 A3 discloses a method for detection of chromosomal translocations, using two or, alternatively, four labels or dyes, which flank the breakpoints of both breakpoints participating in a translocation, distally and proximally. This method offers no possibilities of detecting more than the one translocation in the breakpoint region that is flanked by the probes.

In total, it can therefore be found that with the methods known from the state of the art, it is not possible to efficiently detect multiple chromosome abnormalities at the same time or simultaneously, which are present in cells or tissue, by means of in situ hybridization.

Simultaneous assignment or assignment at the same time, of defined DNA or chromosome regions, within the scope of in situ hybridizations, has been known, until now, only in the case of methods for detection of whole chromosomes having a size, in humans, between about 50 Mbp and 250 Mbp, or larger chromosomal regions, e.g. chromosome arms, using what are called "Whole Chromosome Painting Probes" (WCP) or "Partial Chromosome Painting Probes" (PCP). With the underlying techniques, e.g. mFISH (multiplex FISH), SKY-FISH (spectral karyotyping), multicolor FISH, COBRA-FISH (Combined Binary Ratio labeling FISH) or also 24-color FISH, it is possible to mark and distinguish a total of twenty-four different "Chromosome Painting Probes" using about four to seven different fluorescence dyes. In a similar method, the chromosome-arm-specific probes of all chromosomes can be marked differently, in what is called 42-color-FISH. However, the aforementioned methods are only suitable for cells that are in the metaphase. The aforementioned methods are only possible because only genomic/chromosomal regions in metaphases can be evaluated with the probes used in them, at least essentially without superimposition of chromosomal material. Analysis of cells in the interphase, which generally is required to allow analysis of the genetic material of solid tumors, is not possible with such methods. Furthermore, the probes used in this regard can be detected relatively easily, since they address large regions. Evaluation of these analyses cannot take place manually, i.e. with observation of the signals on the fluorescence microscope, but rather only in computer-based manner, using suitable evaluation software.

The methods and probe compositions for BrISH and FISH in connection with structural and numerical chromosome mutations or chromosome abnormalities, particularly in connection with methods and probe compositions known in the state of the art, with tumors or cancer illnesses, are connected with certain disadvantages. For example, there are no compositions of locus-specific probes and methods that allow reliable, simple, and fast detection and discrimination of multiple potentially different structural and/or numerical chromosome mutations or chromosome abnormalities.

Particularly in the case of the structural chromosome mutations, simultaneous analysis, or analysis at the same time, of multiple different chromosomal mutations, which are not dependent on one another, i.e. do not exchange any chromosomal material or are not reciprocal, is not possible at all, or only possible with great difficulty, particularly in underlying Break-Apart approaches.

The present invention is therefore based on the task of making available a method or a composition that is suitable for detection and analysis of chromosome mutations or chromosome abnormalities, and avoids the disadvantages of the state of the art as described above, at least to a great extent, or at least weakens them.

In particular, the present invention is based on the task of making available a method that makes possible reliable and simultaneous detection of multiple chromosome abnormalities that are different from one another, particularly chromosome abnormalities that are independent of one another (i.e. not reciprocal), particularly in one approach. In the same manner, the present invention is based on the task of making available a method that furthermore also makes assignment of chromosome abnormalities to a specific chromosome region or DNA region possible.

DESCRIPTION

To accomplish the task described above, the present invention proposes a method according to claim 1; further advantageous embodiments are the object of the dependent claims in this regard.

Furthermore, an object of the present invention is a composition for detection of chromosome abnormalities in accordance with the independent claim in this regard, or a composition for use in prophylactic or therapeutic treatment or in diagnosis or prognosis of illnesses connected with chromosome abnormalities.

Yet another object of the present invention is the use of a composition according to the present invention in accordance with the independent claim in this regard.

Furthermore, the present invention relates to use of at least two, particularly at least three, preferably at least four locus-specific hybridization probes, which are different from one another, in accordance with the independent claim in this regard.

Furthermore, an object of the present invention is use of at least one locus-specific hybridization probe marked with at least two detection labels, in accordance with the independent claim in this regard.

Finally, an object of the present invention is a kit or kit of parts or set for detection of chromosome abnormalities; further, advantageous properties are the object of the dependent claim in this regard.

It is understood that in the following, special configurations, embodiments or the like, which are described only in connection with one aspect of the invention, apply analogously also with reference to the other aspects of the invention, without this having to be explicitly mentioned.

Furthermore, it must be noted, in the case of all the relative or percentage amount information, particularly weight-related amount information, that this information is to be selected by a person skilled in the art, within the scope of the present invention, in such a manner that the sum of the respective ingredients, active substances, additives or ancillary substances or the like always come up to 100% or 100 wt.-%. However, this is obvious to a person skilled in the art.

Furthermore, it holds true that a person skilled in the art can deviate from the numerical, range or amount information listed below, depending on the application or an individual case, without departing from the scope of the present invention.

Furthermore, it holds true that all the parameter information or the like indicated below can fundamentally be determined or established using standardized or explicitly indicated determination methods, or, alternatively, using determination methods that are familiar to a person skilled in the art, as such.

To accomplish the task described above, the present invention proposes, according to a first aspect according to the invention, a method for detection of chromosome abnormalities, particularly structural and/or numerical chromosome abnormalities, preferably structural chromosome abnormalities, by means of in situ hybridization, by detection of chromosome regions and/or DNA regions in a biological sample, preferably in one or more cell(s) and/or in one or more cell nucleus/nuclei, wherein the in situ hybridization is carried out as interphase/in situ hybridization, wherein the in situ hybridization is carried out with at least four locus-specific hybridization probes that are different from one another, each marked with a first detection label, wherein in particular for generating at least one mixed signal, at least one of the locus-specific hybridization probes is marked with at least one further detection label, different from the first detection label, with reference to the respective locus-specific hybridization probe, so that a signal pattern is generated, and wherein existing chromosome abnormalities are identified using the signal pattern and/or assigned to a chromosome region and/or DNA region.

In other words, the present invention is based on the basic principle of allowing simultaneous detection or detection at the same time of multiple chromosome abnormalities, which are different from one another, particularly independent of one another, i.e. not reciprocal chromosome abnormalities, in a biological sample, as well as their assignment to a detected chromosome region or DNA region, by means of targeted generation of mixed signals in signal patterns generated by means of interphase/in situ hybridizations.

In particular, it can therefore be provided, within the scope of the present invention, that the chromosome abnormalities are chromosome abnormalities that are independent of one another. Stated in different words, it can be provided, according to the invention, that the chromosome abnormalities are not dependent on one another. Likewise, it can be provided that the chromosome abnormalities are not reciprocal.

According to a special embodiment of the present invention, it is furthermore preferred that the chromosome abnormalities are not connected with reciprocal or mutually dependent chromosome abnormalities or associated with these.

The present invention is connected with numerous advantages and particularities, which are discussed below, in non-restrictive manner, and should be evaluated as an indication of the patentability of the present invention.

Within the scope of the present invention, it was possible, in completely surprising manner, to make available a method for detection of chromosome abnormalities, which allows clear detection of multiple possible structural or numerical chromosome abnormalities, on the one hand, and, on the other hand, clear differentiation between these chromosome abnormalities or clear assignment of the detected chromosome abnormalities to specific chromosome regions or DNA regions in a single hybridization approach, within the scope of interphase/in situ hybridization. In particular, the chromosome abnormalities can be chromosome abnormalities that are independent of one another, which are not mutually dependent and not reciprocal. This was not possible until now in the state of the art, particularly within the scope of interphase/in situ hybridizations.

Using the method according to the invention, it is therefore possible to analyze samples, particularly biological samples to be examined for chromosome abnormalities, such as sections of tissue, particularly tumor tissues, in clearly faster and more efficient manner, since an individual sample can be simultaneously examined, in other words in one approach, for multiple chromosome abnormalities that are different from one another. Furthermore, any chromosome abnormalities that are detected can be assigned to a defined or specific DNA region or chromosome region.

Furthermore, using the method according to the invention, the sample amount required for detection of chromosome abnormalities can be significantly reduced. This is particularly advantageous against the background that removal of tissue for examination purposes, particularly in connection with the diagnosis or recognition or further analysis of cancer illnesses, usually takes place by means of a fine needle biopsy, in the meantime, which only permits taking a limited sample amount, whereas open biopsies, which also allow taking larger amounts of tissue, are performed increasingly rarely.

Furthermore, because of the great efficiency of the method according to the invention, the required amount of materials, such as enzymes, fluorescence dyes and the like, some of which can be cost-intensive, is reduced for carrying out the in situ hybridization, so that the method is also advantageous with regard to economic and ecological aspects.

For a better understanding of the present invention, the central terms and designations of the method according to the invention will be defined below:

According to the invention, the term chromosome abnormalities, synonymously also referred to as chromosome anomalies, is particularly understood to mean structural and numerical chromosome abnormalities. In the case of structural chromosome abnormalities, changes exist in the structure of a chromosome, so that this is also referred to as chromosome mutation. In particular, this can involve inversions, translocations, deletions, segmental duplications, insertions, duplications or amplifications. Numerical chromosome abnormalities, in contrast, lead to a change in the number of chromosomes. Synonymously, the term genome mutation is used. In the case of numerical chromosome abnormalities or genome mutations, these can particularly involve aneuploidies or polyploidy. The method according to the invention is particularly suitable for detection of structural chromosome abnormalities.

The in situ hybridization used according to the invention is based on hybridization or pairing of complementary bases of nucleic acid single strands, particularly DNA single strands, so that specific nucleic acid sequences can be detected in a sample, such as a tissue or a cell preparation. Within the scope of the in situ hybridization, directly or indirectly marked, synthetically produced, particularly locus-specific hybridization probes are hybridized with nucleic acid single strands of the sample, and subsequently detected.

Fundamentally, in situ hybridization can take place or be carried out at different stages of the cell cycle of the cells or cell nuclei being examined, and carrying this out in the metaphase, when the chromosomes are present in the condensed state, or in the interphase, when the chromosomes are present in the de-condensed state, has established itself. Depending on the goal or purpose of the in situ hybridization, it is not always possible to carry it out on condensed chromosomes in the metaphase, particularly, for example, in the examination of cells of solid tumors for chromosome abnormalities. According to the invention, it is therefore provided to carry out the in situ hybridization on cells or cell nuclei that are in the interphase.

Within the scope of the present invention, locus-specific hybridization probes are understood to be probes that are complementary to a specific chromosome region or DNA region or to a certain chromosome region or DNA region of the DNA material or of the genetic material in a sample to be examined. Usually, the hybridization probes used according to the invention are based on nucleic acids or nucleic acid fragments and are able to specifically bind to or hybridize with the chromosome region or DNA region to be detected. The chromosome region or DNA region to be detected can have a variable length. In particular, it can be provided that a chromosome region or DNA region to be detected comprises a single or individual gene, in whole or in part. Likewise, it can also be provided that a chromosome region or DNA region to be detected comprises multiple genes, preferably adjacent genes, preferably two genes, in whole or in part.

As far as the configuration of the hybridization probes, according to the invention, is specifically concerned, it can particularly be provided that a locus-specific hybridization probe is based on multiple, particularly a plurality of nucleic acid fragments (synonymously also probe fragments), which are referred to, in their totality, as a locus-specific hybridization probe. Furthermore, it is possible—although less preferred—that the locus-specific hybridization probes are based on only a single nucleic acid fragment or formed by a single nucleic acid fragment.

Detection labels, within the scope of the present invention, refer to materials or substances that are coupled with nucleic acids or nucleic acid fragments for determination or detection purposes. The selection of suitable detection labels lies within the usual ability of a person skilled in the art and does not require any further explanations at this point. The nucleic acid fragments marked with detection labels and bound to or hybridized with the DNA segment or chromosome segment to be determined or detected, by means of in situ hybridization, can be detected by means of methods known to a person skilled in the art and adapted to the detection label used, directly or indirectly, for example by means of fluorescence microscopy or, particularly after enzymatic reaction or visualization by means of enzymatically reacted dye substrates, by means of bright-field microscopy. In particular, a signal pattern is generated by means of the detection labels at the locus-specific hybridization probes, within the scope of in situ hybridization, which signal pattern serves as the basis for examination of the sample for possible chromosome abnormalities.

Furthermore, the term "detection label," used according to the invention, refers, in the following, to the kind or type of detection label and not to the numerical number of detection label molecules, i.e. formulations such as "at least one detection label" mean a certain type of a detection label or the specific selection of a detection label. The term "multiple detection labels" therefore also relates to the selection of detection labels of different types, which are different from one another, and not to the number of detection label molecules used. It is obvious to a person skilled in the art that within the scope of marking of hybridization probes, these are usually coupled with more than one detection label molecule.

The locus-specific hybridization probes used according to the invention, particularly probe fragments or nucleic acid fragments, therefore hybridize specifically with a selected DNA region or chromosome region of the genetic material in a sample, and, on the basis of the coupled detection label, within the scope of in situ hybridization, generate a signal pattern. Within the scope of the present invention, a signal pattern is understood to be the totality of all the signals generated by means of the in situ hybridization, on the basis of the locus-specific hybridization probes marked with detection labels.

In this connection, it has surprisingly been found, within the scope of the present invention, that well detectable mixed signals, which can furthermore be well distinguished from the other signals, can be generated by means of marking of locus-specific hybridization probes with at least two detection labels in the signal pattern that are different from one another, which signals allow assignment of a chromosome abnormality that has occurred to a detected DNA region or chromosome region. A mixed signal in the sense of the invention is therefore a signal that is generated by at least two, but also by multiple detection labels that are different from one another and situated on a locus-specific hybridization probe. Since mixed signals are generated by the at least two, particularly multiple detection labels of a locus-specific hybridization probe, these are visible in the signal pattern of the in situ hybridization even in the case of chromosome abnormalities and continue to exist even in the case of chromosome abnormalities. Possible embodiments or configurations of the locus-specific hybridization probes for generation of mixed signals will still be explained in detail below.

Preferred embodiments of the method according to the invention will be described in detail below:

According to a first embodiment according to the invention, it can be provided that the first detection labels of the locus-specific hybridization probes used are the same in each instance. According to a second, equally preferred embodiment according to the invention, it can be provided that the locus-specific hybridization probes used are marked with first detection labels that are different from one another, in each instance.

In other words, it can be provided, according to the invention, that the locus-specific hybridization probes used—simply as an example and not restrictively—have the same fluorescence dye or the same hapten, for example, as the first detection label.

Likewise, the locus-specific hybridization probes used can have fluorescence dyes that are different from one another, haptens that are different from one another or the like as the first detection label, in each instance, again as an example and not restrictively. Marking with first detection labels that are different from one another has proven to be advantageous particularly with regard to detection of chromosome abnormalities that go along with chromosome breaks, such as translocations or inversions.

As far as detection of chromosome abnormalities, according to the invention, is furthermore concerned, it is preferred, according to the invention, that at least one, particularly multiple chromosome abnormalities that are different from one another is/are detected and/or determined from among the plurality of possible chromosome abnormalities in the sample.

Likewise, it can be provided that at least two, particularly multiple chromosome abnormalities that are different from one another are detected in the sample from among a plurality of possible chromosome abnormalities, at the same time, particularly simultaneously.

According to a further preferred embodiment of the present invention, it can be provided that the method according to the invention is carried out as a multiplex method for simultaneous detection of multiple chromosome abnormalities that are different from one another.

A particular advantage—as was already explained above—of the method according to the invention as compared with the methods for detection of chromosome abnormalities by means of in situ hybridization that are known in the state of the art therefore lies in the fact that now, even samples, particularly on the basis of cells or cell nuclei that are in the interphase, can be examined in a single hybridization approach, simultaneously or at the same time, for multiple possible chromosome abnormalities, with assignment of these abnormalities to a specific DNA region or chromosome region.

In this connection, it can particularly be provided that chromosome abnormalities are identified in the signal pattern by means of the at least one mixed signal, particularly multiple mixed signals, and assigned to the chromosome regions and/or DNA regions to be detected. In this regard, reference is particularly made to FIG. 7, in which the detection, according to the invention, of chromosome abnormalities in the form of amplifications can be seen, as an example. According to FIG. 7, four different chromosome regions are examined, wherein four hybridization probes that are different from one another, of which three are marked with at least one further detection label for generating specific mixed signals, are used (cf. FIG. 7 a)). On the basis of the marking of three of the four chromosome regions with a specific mixed signal, in each instance, the "cluster" generated by means of amplification of a detected chromosome region in the signal pattern can be assigned to a hybridization probe or a detected chromosome region (cf. FIG. 7 b)).

According to the invention, it can therefore be particularly provided that marking of further locus-specific hybridization probes with the at least one further detection label takes place in such a manner that the locus-specific hybridization probes marked with at least one further detection label generate mixed signals in the signal pattern that are different from one another, in each instance.

Likewise, it can be provided—particularly for the case that chromosome abnormalities that do not result from chromosome breaks, such as amplifications or deletions, are supposed to be detected—that marking of further locus-specific hybridization probes with at least one further detection label takes place in such a manner that a mixed signal that is specific for a chromosome region and/or DNA region is generated in the signal pattern by means of every locus-specific hybridization probe marked with at least one further detection label. In this connection, it is therefore preferred, within the scope of the present invention, if each region detected by means of a locus-specific hybridization probe can be assigned to a specific signal, particularly a mixed signal, within the signal pattern.

Furthermore it is preferred, according to the invention, if marking of further locus-specific hybridization probes with the at least one further detection label takes place in such a manner that each chromosome abnormality to be detected in the signal pattern is assigned to a detected chromosome region and/or DNA region, using a specific mixed signal.

As far as the number of locus-specific hybridization probes marked with at least one further detection label is concerned, this number is variable and depends, in particular, on the number of chromosome abnormalities to be detected or to be examined:

According to the invention, it is preferred if at least two, particularly at least three, preferably at least four, preferentially at least five, particularly preferentially at least six, very particularly preferentially at least seven further locus-specific hybridization probes are marked with at least one further detection label that is different from the first. Likewise, it can be provided that mixed signals specific for a chromosome region and/or DNA region are generated in the signal pattern by means of at least two, particularly at least three, preferably at least four, preferentially at least five, particularly preferentially at least six, very particularly preferentially at least seven further locus-specific hybridization probes.

This method of procedure, described above, is particularly suitable for the case that chromosome abnormalities that do not result from chromosome breaks, such as amplifications or deletions, are supposed to be detected. On the basis of an increase in the number of hybridization probes marked with at least one further detection label, preferably multiple detection labels, which probes generate an individual mixed signal, in each instance, the number of chromosome abnormalities to be detected or determined simultaneously can therefore also be increased.

According to a further, special embodiment of the present invention, it is furthermore possible to detect chromosome abnormalities that result from chromosome breaks, such as, for example, translocations or inversions, and to assign them to a specific chromosome region or DNA region:

According to this embodiment according to the invention, it can be provided that two locus-specific hybridization probes, in each instance, flank a chromosome segment, particularly a breakpoint region, wherein the locus-specific hybridization probes that flank a chromosome segment, particularly a breakpoint region, are marked with detection labels that are different from one another, so that a fusion signal is generated in the signal pattern by means of the locus-specific hybridization probes that flank a chromosome segment, in each instance, particularly a breakpoint region, particularly for the case that no chromosome abnormality is present.

In this connection, "flank" preferably means that the specific end of a hybridization probe that comes closest to the chromosome segment or breakpoint region hybridizes with a base that has a distance of 0 to 1 Mbp from the chromosome segment or breakpoint region, particularly a distance of 0 to 500 kb, preferably a distance of 0 to 100 kb, preferentially a distance of 0 to 10,000 bp, and particularly preferentially a distance of 0 to 1,000 bp.

In other words, it is provided, according to this embodiment of the present invention, that the DNA regions or chromosome regions to be detected are situated distally and proximally relative to specific selected chromosome segments, particularly potential breakpoint regions on a chromosome. In this regard, it can particularly be provided that either the chromosome segment that is situated distally or the one situated proximally is detected using at least one further hybridization probe marked with a detection label that is different from the first detection label.

Within the scope of the present invention, a breakpoint region is understood to be those regions of a chromosome that can be affected by chromosome breaks. As a consequence of chromosome breaks, chromosome abnormalities on the basis of structural rearrangements can come about, particularly translocations or inversions. Chromosome abnormalities are known for a number of illnesses, which abnormalities are illness-specific, in each instance, and based on chromosome breaks, particularly translocations or inversions. Using the method according to the invention, multiple, particularly known breakpoint regions can be examined in the genetic material of a sample, particularly a tissue sample, for the presence of chromosome abnormalities.

In this embodiment according to the invention, a fusion signal is therefore produced by means of the two locus-specific hybridization probes that flank a breakpoint region, in each instance, which signal is generated on the basis of the two detection labels of the first and second locus-specific hybridization probe, which are different from one another, particularly for the case that no chromosome abnormality is present.

In contrast to the mixed signals already described above, which are generated by different detection labels of a locus-specific hybridization probe, fusion signals are generated by means of locus-specific hybridization probe that are different from one another, which are present in the immediate vicinity of one another, hybridized onto the genetic material or the DNA in the sample.

In other words, within the scope of the method according to the invention, a fusion signal is generated, for the case that no chromosome abnormality is present at a flanked breakpoint, and the locus-specific hybridization probes that are used hybridize with the genetic material or the DNA in the sample, in the immediate vicinity. If, in contrast, a chromosome abnormality is present in the region, the locus-specific hybridization probes used can no longer bind in the immediate vicinity on the basis of the structural rearrangements of a DNA segment. In place of a fusion signal, two individual signals (synonymously also "split signal"), which are preferably different from one another, are detected in the signal pattern.

Furthermore, the hybridization probes marked with the at least one further detection label, different from the first detection label, generate mixed signals on the basis of the first detection label and the at least one further detection label of the respective hybridization probe. These can therefore form a mixed signal and fusion signal in the signal pattern, together with a second hybridization probe that flanks a chromosome segment, particularly a breakpoint region, in the event that no chromosome abnormality is present. In the case of chromosome abnormalities, in contrast, a single signal as well as a single signal that is accompanied by a mixed signal are generated in the signal pattern, on the basis of the hybridization probes that flank a chromosome segment, particularly a breakpoint region, in normal cells or normal cell nuclei, one of which probes is marked with at least one further detection label.

Within the scope of the present invention, it is therefore possible to assign chromosome abnormalities defined using the mixed signal, on the basis of the locus-specific hybridization probes marked with at least one further detection label, to breakpoint regions or detected chromosome regions or DNA regions.

According to the invention, it is therefore preferred if, in each instance, the hybridization probe marked with at least one further detection label, different from the first, generates a mixed signal and fusion signal in the signal pattern, together with the second locus-specific hybridization probe, which flanks a chromosome segment, particularly a breakpoint region, particularly for the case that no chromosome abnormality is present.

Furthermore, it can be provided that the hybridization probe marked with at least one further detection label, different from the first, and the second locus-specific hybridization probe that flanks a chromosome segment, particularly a breakpoint region, generate a single signal in the signal pattern, in each instance, particularly wherein the hybridization probe marked with the at least one further detection label furthermore generates a mixed signal in the signal pattern, particularly for the case that a chromosome abnormality is present.

In particular, it can therefore be provided, within the scope of the method according to the invention, that in the signal pattern, chromosome abnormalities are assigned to a detected chromosome region and/or DNA region and/or a chromosome segment, particularly a breakpoint region, by means of mixed signals.

According to this preferred embodiment of the method according to the invention, it is therefore possible to simultaneously depict or mark a series of potential breakpoint regions in a single sample by means of interphase/in situ hybridization. For the case that no chromosome abnormality has taken place at the marked breakpoints, fusion signals are generated in the signal pattern, whereas the occurrence of single signals or split signals indicates the presence of chromosome abnormalities. Abnormal single signals or split signals can be assigned to a specific hybridization probe and therefore to a specific breakpoint region on the basis of the additionally generated mixed signal (cf. FIG. 1).

In particular, it can be provided, within the scope of the present invention, that at least six, preferably at least eight, preferentially at least ten, particularly preferentially at least twelve, even more preferentially at least fourteen different locus-specific hybridization probes are used, wherein two locus-specific hybridization probes, in each instance, flank a chromosome segment, particularly a breakpoint region, in each instance, and that at most twenty-four different locus-specific hybridization probes are used, wherein two locus-specific hybridization probes flank a chromosome segment, particularly a breakpoint region, in each instance.

Furthermore, it is preferred, according to the invention, if marking of further locus-specific hybridization probes with at least one further detection label, different from the first, takes place in such a manner that each flanked chromosome segment, particularly breakpoint region, and/or each chromosome region and/or DNA region to be detected can be identified and/or assigned in the signal pattern, using fusion signals and mixed signals.

In this connection, it is particularly preferred, according to the invention, if a first breakpoint region to be examined is flanked by two hybridization probes, which have only one detection label, in each instance, so that this breakpoint region is visible in the signal pattern only by means of a fusion signal or two single signals or split signals. In contrast, a specific or individual mixed signal is assigned to each further breakpoint region to be examined, by means of marking of at least one of the two flanking hybridization probes with at least one further detection label in the signal pattern, so that in the signal pattern, in total a plurality of chromosome regions or DNA regions, particularly breakpoint regions, can be depicted in distinguishable manner.

According to a particularly preferred embodiment of the method according to the invention, it can be provided that (a) a first locus-specific hybridization probe marked with a detection label A and a second locus-specific hybridization probe marked with a detection label B flank a chromosome segment, particularly a breakpoint region and generate a fusion signal A-B in the signal pattern generated by means of in situ hybridization, b) 2 to 12 further locus-specific hybridization probes flank up to six further chromosome segments, particularly breakpoint regions, wherein also, one of the two locus-specific hybridization probes flanking a chromosome segment, particularly a breakpoint region, is marked with a detection label A, in each instance, and one of the two locus-specific hybridization probes that flank a chromosome segment, particularly a breakpoint region, in each instance, is marked with a detection label B, so that the locus-specific hybridization probes that flank a chromosome segment, particularly a breakpoint region, generate a fusion signal A-B in the signal pattern generated by means of in situ hybridization, and (c) at least one, preferably multiple locus-specific hybridization probe(s) is/are marked with at least one further detection label X, so that the locus-specific hybridization probes marked with at least one further detection label generate fusion signals and mixed signals A-B/X in the signal pattern generated by means of in situ hybridization, wherein the fusion signals and mixed signals A-B/X generated by means of in situ hybridization change to mixed signals A/X and/or B/X in the case of chromosome abnormalities, and/or wherein the fusion signals A-B change to single signals A and/or B in the signal pattern generated by means of in situ hybridization in the case of chromosome abnormalities, so that chromosome abnormalities are assigned to a chromosome region and/or DNA region and/or to a chromosome segment, particularly a breakpoint region, flanked by two locus-specific hybridization probes, using the signal pattern generated by means of in situ hybridization.

As far as the detection label X provided in the embodiment described above is furthermore concerned, this can be formed by a single detection label, particularly a detection label $X_1$.

Furthermore, it can be provided that the detection label X is formed by multiple detection labels that are different from one another, preferably selected from the group of detection labels $X_1$, $X_2$, . . . and/or $X_n$, wherein the index "n" represents a natural whole number from 1 to 20, particularly 1 to 10, preferably 1 to 5. In this regard, it can furthermore be provided that the detection labels $X_1$, $X_2$, . . . and/or $X_n$ are used to generate mixed signals that are different from one another, particularly specific mixed signals in different ratios to one another.

According to a further embodiment, it is also possible that the detection label X is formed by multiple detection labels, different from one another, preferably selected from the group of detection labels $X_1$, $X_2$, $X_3$, $X_4$, $X_5$ and/or $X_6$. In this connection, it is preferred if the detection labels $X_1$, $X_2$, $X_3$, $X_4$, $X_5$ and/or $X_6$ are used for generating mixed signals that are different from one another, particularly specific mixed signals in different ratios to one another.

Within the scope of the present invention it has therefore surprisingly been possible for a plurality of mixed signals to be generated, even on the basis of a few individual detection labels, in that in order to generate mixed signals, the locus-specific hybridization probes having at least one further detection label are marked with multiple detection labels that are different from one another, for generation of mixed signals.

In particular, it can be provided, according to the invention, that for generation of mixed signals within the scope of marking of locus-specific hybridization probes, multiple, particularly two to six detection labels that are different from one another, are used in (amount) ratios that differ from one another, in each instance. As an example—and by no means restrictively—a locus-specific hybridization probe can have three further detection labels—aside from the first detection label, wherein in this regard, the proportion of the first detection label amounts to 20%, the proportion of the second detection label amounts to 60%, and the proportion of the third detection label amounts to 20%, with reference to the three further detection labels.

According to yet another embodiment of the present invention, it can furthermore be provided that (a) a first locus-specific hybridization probe marked with a detection label A and a second locus-specific hybridization probe marked with a detection label B flank a first chromosome segment, particularly a first breakpoint region, and generate a fusion signal A-B in the signal pattern generated by means of in situ hybridization, (b) a third locus-specific hybridization probe marked with a detection label A and a fourth locus-specific hybridization probe marked with a detection label B flank a second chromosome segment, particularly a second breakpoint region, and generate a fusion signal A-B in the signal pattern generated by means of in situ hybridization, and (c) the third locus-specific hybridization probe and/or the fourth locus-specific hybridization probe is/are marked with a further detection label $X_1$, and generate fusion signals and mixed signals A-B/$X_1$ in the signal pattern generated by means of in situ hybridization, wherein in the signal pattern, chromosome abnormalities of the first chromosome segment, particularly the first breakpoint region, are identified by means of single signals A and/or B and/or wherein chromosome abnormalities of the second chromosome segment, particularly the second breakpoint region, are identified by means of mixed signals A/$X_1$ and/or B/$X_1$ and/or assigned to the second chromosome segment, particularly the second breakpoint region.

As far as the method of procedure for analysis of chromosome abnormalities in the signal pattern generated by means of in situ hybridization is concerned, it has proven to be particularly efficient if, in a first step, the fusion signals generated by the first detection labels are detected and/or analyzed, and in a subsequent step, in the case of occurrence of single signals, detection and/or analysis of the mixed signals and their assignment to the detected chromosome regions and/or DNA regions takes place.

In particular, this can take place in that first, during the analysis of the signal pattern, a filter is used by means of which only the signals generated by the first detection labels, i.e. the fusion signals or potential single signals are visible. Since chromosome abnormalities that require further analysis are present only when single signals occur in the signal pattern, the mixed signals on the basis of which—seen in conjunction with the position of the fusion signals or single signals in the signal pattern—chromosome abnormalities can be assigned to a specific chromosome region or DNA region are also depicted particularly by means of the use of a different filter, particularly a filter suitable for depicting the mixed signals.

Furthermore, according to a special embodiment of the method according to the invention, it can be provided that detection of the signal pattern takes place by means of computer-assisted analysis. This is particularly advantageous if, for generation of mixed signals, hybridization probes are marked with more than at least one further detection label, preferably at least two further, preferably multiple further detection labels in different or defined ratios to one another. Computer-assisted analyses also allow differentiation of mixed signals on the basis of measurements of the underlying color components or colors, which it would not be possible to distinguish from one another with the naked eye when looking at them under the fluorescence microscope.

According to the invention, it can therefore particularly be provided that detection of translocations or inversions takes place using up to twenty-four locus-specific hybridization probes, wherein two locus-specific hybridization probes, in each instance, flank a respective breakpoint region distally and proximally, and individual locus-specific hybridization probe of these probe pairs are simultaneously marked with further detection labels. Preferably, therefore, up to twelve different breakpoint regions can be examined in one approach, with up to twelve different Break-Apart approaches, for depiction of up to twelve translocations or inversions. Detection of a specific translocation takes place by way of identification of the separations of the probe pairs or of the fusion signals of the probe pairs, and using the respective mixed colors or mixed signals.

It is also possible to detect translocations and inversions using up to twenty-four locus-specific hybridization probes, wherein two probes, in each instance, flank a respective breakpoint region distally and proximally, and these probe pairs are marked, in each instance, with the same labels A and B, wherein one probe is marked with label A and the other probe is marked with label B, in each instance, and individual probes of these probe pairs are simultaneously marked with further detection labels X. Detection of a specific translocation and/or inversion takes place by way of changing specific fusion signals and mixed signals A-B/X in the case of a chromosome abnormality to new and separate mixed signals A/X and/or B/X. In this regard, it is also possible to use no further label X in the case of one probe pair, so that the usual separate signals A and/or B occur only for this probe pair in the case of the underlying abnormality.

Thus it is also possible, for the first time, that in a first analysis of multiple different potentially detectable structural chromosome mutations, only of the signals A and B, using specific filter systems, e.g. double filters for the signals A and B, which make only the signals A and B but not further labels X visible, a statement can first rapidly be made whether Break Apart of the fusion signals A-B has taken place at all, and, in general, whether a translocation or inversion is present. Only in the event of positive occurrence of separate signals A and/or B does an evaluation of the mixed signals then take place, with the involvement of the labels X, and thereby clear assignment of the underlying translocation takes place.

In the following, further particularities or embodiment possibilities of the method according to the invention will furthermore be described, which apply analogously for all the possible embodiments of the method according to the invention as described above:

As far as the single chromosome regions or DNA regions to be detected by a single locus-specific hybridization probe, in each instance, are concerned, these preferably have a length of less than 5 Mbp, particularly less than 2 Mbp, preferably less than 1 Mbp, preferentially less than 750 kbp, particularly preferentially less than 500 kbp within the scope of the present invention. Likewise, it can be provided that the chromosome region and/or DNA region to be detected by a single locus-specific hybridization probe has of at least 500 bp, particularly at least 1 kbp, preferably at least 5 kbp, preferentially at least 10 kbp. Finally, it can also be provided that the chromosome region and/or DNA region to be detected by a single locus-specific hybridization probe has a length in the range from 500 bp to 5 Mbp, particularly in the range from 1 kbp to 2 Mbp, preferably in the range from 5 kbp to 1 Mbp, preferentially in the range from 10 kbp to 750 kbp, particularly preferentially in the range from 10 kbp to 500 kbp.

Furthermore, as far as the further embodiment of the locus-specific hybridization probes used according to the invention is concerned, these are preferably present in the form of nucleic acid fragments, particularly in the form of polynucleotides, modified polynucleotides, modified nucleic acid fragments, oligonucleotides and/or oligonucleotides. Specifically, as far as the modified nucleic acid fragments are concerned, these can particularly be locked nucleic acids (LNA) or peptide nucleic acids (PNA).

According to a first embodiment of the present invention, it can furthermore be provided that the locus-specific hybridization probes are formed, in each instance, by a single nucleic acid fragment, which covers the chromosome region and/or DNA region to be detected, in each instance.

According to another and furthermore preferred embodiment of the present invention, it can also be provided that the locus-specific hybridization probes are formed, in each instance, by a plurality of nucleic acid fragments ("probe fragments"), which cover the chromosome region and/or DNA region to be detected, in each instance. In this regard, it is furthermore preferred if the individual nucleic acid fragments ("probe fragments") of a locus-specific hybridization probe have a length in the range from 5 to 2,000 bp, particularly in the range from 10 to 1,500 bp, preferably in the range from 50 to 1,000 bp.

Furthermore, as far as the generation of mixed signals by means of marking of locus-specific hybridization probes with at least one further detection label, different from the first detection label, for targeted generation of mixed signals is concerned, this can take place in different ways:

According to a first embodiment of the present invention, in this regard, it can be provided that for generation of mixed signals, the nucleic acid fragments ("probe fragments") of a locus-specific hybridization probe are marked, along with the first detection label, with a further detection label that is different from the first detection label. Hybridization probes marked in this manner therefore generate a mixed signal, which is based only on two detection labels that are different from one another.

Furthermore, it can be provided, according to a further embodiment of the present invention—particularly against the background of increasing the bandwidth of specific mixed signals or increasing the number of specific mixed signals, i.e. signals that can be differentiated from one another—that for generation of mixed signals, the nucleic acid fragments ("probe fragments") of a locus-specific hybridization probe are marked, along with the first detection label, with multiple, particularly two to twenty, preferably two to ten, preferentially two to six detection labels that are different from the first detection label. In this regard, it can particularly be provided that the detection labels are used in amounts that are different from one another.

According to the invention, it can therefore be provided that for generation of mixed signals within the scope of marking of locus-specific hybridization probes, multiple detection labels that are different from one another are used in ratios that are different from one another, in each instance. For example—and by no means restrictively—a locus-specific hybridization probe can have three further detection labels—aside from the first detection label—wherein the proportion of the first detection label amounts to 20%, the proportion of the second detection label amounts to 60%, and the proportion of the third detection label amounts to 20% with reference to the three further detection labels.

According to this embodiment, it can therefore be provided that the hybridization probes have at least two, preferably multiple detection labels that are different from one another, along with the first detection label. By means of the use of different detection labels in ratios that are different from one another, the number of specific mixed signals, particularly signals that can be distinguished from one another, can be increased, in total, and this in turn makes detection of a greater number of detectable chromosome abnormalities possible.

Within the scope of marking of locus-specific hybridization probes it can be provided according to the invention, furthermore fundamentally, that individual nucleic acid fragments of a hybridization-specific probe are marked with only one detection label. In this regard, this can be the first detection label and/or any further detection label (cf. FIG. 2 I)).

To state it differently, it is therefore possible, according to the invention, that a first portion of the nucleic acid fragments of a locus-specific hybridization probe is marked only with the first detection label, and further portions of the nucleic acid fragments of a locus-specific hybridization probe are marked, in each instance, with a further detection label that is different from the first detection label. Generation of mixed signals can therefore take place, according to an embodiment of the present invention, in that the detection labels for the mixed signal, which labels are different from one another, are present on nucleic acid fragments of a hybridization-specific probe that are different from one another (cf. FIG. 2 I)).

Furthermore, it can be provided that individual nucleic acid fragments of a hybridization-specific probe are marked with multiple detection labels, which are different from one another, particularly wherein this can involve the first detection label and/or any further detection label (cf. FIG. 2 II)).

According to this embodiment of the present invention, it can therefore be provided that the detection labels that form the mixed signal and are different from one another are present on the same nucleic acid fragments of a hybridization-specific probe or are jointly present on the nucleic acid fragments of a hybridization-specific probe (called a "mixed probe") (cf. FIG. 2 II)).

Furthermore, it can also be provided, within the scope, to combine the two aforementioned embodiments for generation of mixed signals with one another, i.e. that one part of the nucleic acid fragments of a locus-specific hybridization probe that form a mixed signal is marked with only one detection label, and a further or multiple further part(s) of the nucleic acid fragments of a hybridization-specific probe is/are marked with at least two different detection labels.

Furthermore, it is also possible that mixed signals are generated if a spacing of maximally 3 Mbp, particularly maximally 2.5 Mbp, preferably maximally 2 Mbp, preferentially maximally 1 Mbp, particularly preferentially maximally 500 kb, even more preferentially maximally 200 kb is present between individual hybridized nucleic acid fragments of a locus-specific hybridization probe marked with at least one further detection label. To state it differently, it is therefore also possible, according to the invention, to generate a mixed signal if a "gap" of maximally 3 Mbp, particularly maximally 2.5 Mbp, preferably maximally 2 Mbp, preferentially maximally 1 Mbp, particularly preferentially maximally 500 kb, even more preferentially maximally 200 kb is present between the individual hybridized nucleic acid fragments of a locus-specific hybridization probe in the hybridized state, marked with at least one further detection label (cf. FIG. 2 III)).

Therefore mixed signals can particularly be generated by means of the use of "mixed labels" of a single probe. In particular, for the creation of the mixed signals that are specific for a chromosomal region or a genomic segment, it is possible that optionally, i) all the fragments of a probe or optionally also only individual fragments of a probe are marked with multiple labels or II) the same fragments are marked with different labels, in each instance, or III) alternating fragments are marked with different labels, so that here, too, finally only one mixed signal is visible or detectable (cf. FIG. 2 I to III)).

Mixed labels and mixed signals in the sense of the method according to the invention can also occur, in this regard, if individual fragments or all of the fragments previously mentioned under I) to III) overlap only in part.

Mixed labels can also occur, in the sense of the method according to the invention, if individual fragments or fragment groups of a probe, which are marked with at least one label, and other individual fragments or fragment groups of the probe, which are marked with at least one further label, have a spacing of 2 Mbp, optionally 1 Mbp, optionally 500 kb, and optionally 200 kb.

Mixed labels and mixed signals in the sense of the method according to the invention can therefore also occur if two or more probes having the same sequence or almost the same sequence are used, i.e. two or more probes address the same specific chromosomal regions or the same genomic segments, but are marked with different labels, wherein the said probes can also agree only by 95%, optionally 90%, optionally 80%, optionally 70%, optionally 60%, optionally 50%, wherein differences occur either due to sequence variations of fundamentally similar sequences or due to partial overlap of only individual regions of the probes.

The selection of suitable detection labels as such for implementation lies within the usual ability of a person skilled in the art and takes place as a function of the method used for carrying out the in situ hybridization. Usually, direct or indirect marking of the hybridization probes can take place by means of the selection of suitable detection labels.

Particularly good results are obtained, within the scope of the present invention, if the detection labels are selected from the group of dyes; dye substrates; chemiluminescence dyes, particularly acridinium; radioisotopes; Spin labels; enzymes, particularly alkaline phosphatase, horseradish peroxidase, soybean peroxidase and/or beta-galactosidase; haptens, particularly digoxigenin, biotin, 2,4-dinitrophenol, 5(6)-carboxyfluorescein, rhodamine, bromine deoxyuridine, acetylaminofluorene, trinitrophenol, trinitrophenol derivatives, estradiol and/or 2,4-dinitrophenol; Quantum Dots; beads; aminohexylene; pyrenes; and/or fluorescence dyes, particularly fluorescein, fluorescein derivative, 5(6)-carboxyfluorescein, coumarin, coumarin derivative, rhodamine, rhodamine derivative, tetramethyl rhodamine, lissamine, Texas Red, AMCA, TRITC, IR dye, Alexa dye, Dyomics dye, phycoerythrin, Cascade Blue, Oregon Green 488, Pacific Blue and/or Rhodamine Green.

As far as carrying out the in situ hybridization as such is concerned, this can take place in different ways.

In particular, it can be provided, according to a first preferred embodiment of the in situ hybridization, that this takes place with direct marking of the hybridization probes, particularly by means of fluorescence/in situ hybridization (FISH).

Likewise, it can be provided that the in situ hybridization takes place with marking of the hybridization probes with fluorescence dyes, particularly for the visible, infrared and/or ultraviolet emission range, preferably for the emission regions green, orange/red, red, gold and/or blue.

According to a further preferred embodiment of the in situ hybridization, it can likewise be provided that it takes place with indirect marking of the hybridization probes, particularly by means of bright-field/in situ hybridization (BrISH).

Furthermore, it can be provided, according to the invention, that the in situ hybridization takes place with marking of the hybridization probes using haptens, particularly biotin, digoxigenin and/or DNP, and subsequent detection by means of antibody-coupled alkaline phosphatase, antibody-coupled peroxidase and/or antibody-coupled beta-galactosidase.

As far as analysis of fluorescence-based in situ hybridizations is concerned, this preferably takes place using specific individual or multiple filter sets, which particularly allow targeted depiction of fusion signals and mixed signals.

Furthermore, it can be advantageous, particularly in the generation of mixed signals on the basis of more than at least one further detection label, particularly in the generation of mixed labels on the basis of at least two further, preferably multiple further detection labels in different or defined ratios to one another, to undertake an evaluation by means of computer-assisted analysis. Furthermore, it can also be provided to make available superimposed images, particularly by means of computer-assisted analysis, which images allow joint depiction of the signal patterns of different individual or multiple filter sets.

Fundamentally, it is possible to detect a large number of different types of chromosome abnormalities using the according to the invention. In particular, the method according to the invention can be used for detection of translocations, inversions, segmental duplications, deletions, insertions, duplications, aneuploidies and amplifications, particularly translocations and/or inversions.

Within the scope of the method according to the invention, it can be provided, in this regard, that the chromosome abnormalities are connected with illnesses, particularly malignancies, preferably carcinomas, sarcomas and/or leukemias.

The genes to be examined for potential chromosome abnormalities are preferably selected from the group of ALK, ROS1, RET, NRG1, NTRK1, CARS, EML4, FGFR2, FGFR3, KIF5B, TGF, BCR, ABL, ALK, BCL2, BCL6, BIRC3, CCND1, EGR1, ETV6, FGFR1, FGFR3, IGH, KMT2A, MYC, PML, RARA, RUNX1, RUNX1T1, EWSR1, CHOP, FUS, COL1A1, DDIT3, JAZF1, NR4A3, FOX01, FUS, PAX3, PAX7, PDGFB, SS18, TFE3, USP6, WT1, HER2/ERBB2, FGFR1, ALK, CCND1, CDK4, CD274, PDCD1LG2, EGR1, EGFR, ESR1, ETV1, FGF3, 4,19, FGFR2, FGFR3, FHIT (RCC), KRAS, MDM2, MDM4, MET, MYB, MYC, MYCN, PIK3CA, PTEN, SMARCB1, SOX2, TERT, TOP2A, TP53, TYMS and/or VHL.

Particularly good results are achieved, within the scope of the method according to the invention, if the method according to the invention is used for detection of inversions and/or translocations:

Within the scope of a preferred embodiment of the present invention, the method according to the invention is used for detection of different translocations and/or inversions, particularly in lung tumors, wherein in particular, the genes ALK, ROS1, RET, NRG1, NTRK1, CARS, EML4, FGFR2, FGFR3, KIF5B and/or TGF are affected.

Furthermore, it can be provided that the method according to the invention is used for detection of different translocations and/or inversions, particularly in lymphomas and leukemias, wherein in particular, the genes BCR, ABL, ALK, BCL2, BCL6, BIRC3, CCND1, EGR1, ETV6, FGFR1, FGFR3, IGH, KMT2A, MYC, PML, RARA, RUNX1 and/or RUNX1T1 are affected.

According to a further preferred embodiment of the present invention, the method according to the invention is used for detection of different translocations and/or inversions, particularly in sarcomas, wherein in particular, the genes EWSR1, CHOP, FUS, COL1A1, DDIT3, JAZF1, NR4A3, FOX01, FUS, PAX3, PAX7, PDGFB, SS18, TFE3, USP6 and/or WT1 are affected.

It can also be provided, according to the invention, that the method according to the invention is used for detection of inversions and/or translocations, wherein in particular, the genes ALK and ROS1 are affected.

Furthermore, within the scope of the present invention, excellent results are achieved if the method according to the invention is used for detection of amplifications and/or deletions:

For detection of amplifications or deletions, up to twenty-four different locus-specific probes can be used, wherein each probe addresses a respective genomic region, and wherein the different probes marked with different labels in different combinations and ratios. On the basis of the resulting mixed signals in the signal pattern, the different locus-specific probes can be clearly distinguished from one another. Therefore up to twenty-four different amplification events and/or deletion events of the genomic regions in question can be examined using a single method. Detection of a specific amplification or deletion takes place by way of counting out the different mixed signals or mixed colors.

Preferably, the method according to the invention is used for detection of different amplifications and deletions, particularly in breast tumors, colon tumors, and lung tumors, wherein in particular, the genes HER2/ERBB2, FGFR1, ALK, CCND1, CDK4, CD274, PDCD1LG2, EGR1, EGFR, ESR1, ETV1, FGF3,4,19, FGFR2, FGFR3, FHIT (RCC), KRAS, MDM2, MDM4, MET, MYB, MYC, MYCN, PIK3CA, PTEN, SMARCB1, SOX2, TERT, TOP2A, TP53, TYMS and/or VHL are affected.

In total, it was therefore surprisingly found, within the scope of the present invention, that when using locus-specific probes with mixed labels, mixed signals that can be detected well and in a manner that allows them to be evaluated occur, which signals allow clear identification of chromosomal regions affected by an abnormality. The method according to the invention therefore allows detection, for the first time and in surprising manner, of multiple, different structural and/or numerical chromosome mutations. This is not possible with the state of the art.

A further object of the present invention, according to a second aspect according to the invention, is a composition for detection of chromosome abnormalities, particularly structural and/or numerical chromosome abnormalities, preferably structural chromosome abnormalities, by means of in situ hybridization, particularly by means of detection of chromosome regions and/or DNA regions in a biological sample, preferably in one or more cell(s) and/or in one or more cell nucleus/nuclei, particularly by means of a method according to one of the preceding claims, wherein the composition comprises at least two, particularly at least three, preferably at least four locus-specific hybridization probes that are different from one another and each marked with a first detection label, and wherein at least one of the locus-specific hybridization probes is marked with at least one further detection label, different from the first, with reference to the respective locus-specific hybridization probe.

Likewise, according to this aspect according to the invention, a composition for use in prophylactic and/or therapeutic treatment and/or in the diagnosis and/or prognosis of illnesses that are connected with chromosome abnormalities, particularly malignancies, preferably carcinomas, sarcomas and/or leukemias, particularly preferentially lung tumors, lymphomas, leukemias, sarcomas, mammary carcinomas and/or colon cancer, is an object of the present invention, wherein the composition comprises at least two, particularly at least three, preferably at least four locus-specific hybridization probes that are different from one another and are each marked with a first detection label, and wherein at least one of the locus-specific hybridization probes is marked with at least one further detection label, different from the first, with reference to the respective locus-specific hybridization probe.

In this connection, it can particularly be provided that the compositions according to the invention are intended or used for carrying out a method as it was described above.

With regard to further details regarding this aspect of the invention, reference can be made to the above explanations regarding the other aspects according to the invention, which apply analogously also with regard to this aspect of the invention.

Furthermore, an object of the present invention—in accordance with a third aspect according to the invention—is the use of a composition, particularly as it was described above, for detection of chromosome abnormalities, particularly structural and/or numerical chromosome abnormalities, preferably structural chromosome abnormalities, by means of in situ hybridization, particularly by means of detection of chromosome regions and/or DNA regions in a biological sample, preferably in one or more cell(s) and/or in one or more cell nucleus/nuclei, particularly by means of the method described above.

With regard to further details regarding this aspect of the invention, reference can be made to the above explanations regarding the other aspects according to the invention, which apply analogously also with reference to this aspect of the invention.

A further object of the invention is furthermore—according to a fourth aspect according to the invention—the use of at least two, particularly at least three, preferably at least four locus-specific hybridization probes that are different from one another and marked with a first detection label, wherein at least one of the locus-specific hybridization probes is marked with at least one further detection label, different from the first, with reference to the respective locus-specific hybridization probe, for detection of chromosome abnormalities, particularly structural and/or numerical chromosome abnormalities, by means of in situ hybridization, particularly by means of detection of chromosome regions and/or DNA regions in a biological sample, preferably in one or more cell(s) and/or in one or more cell nucleus/nuclei, preferably by means of a method as it was described above.

Likewise, an object of the present invention, according to this aspect of the invention, is the use of at least two, particularly at least three, preferably at least four locus-specific hybridization probes, each marked with a first detection label, wherein at least one of the locus-specific hybridization probes is marked with at least one further detection label, different from the first, with reference to the respective locus-specific hybridization probe, preferably within the scope of a previously described method according to the invention, in the diagnosis and/or prognosis of illnesses connected with chromosome abnormalities, particularly malignancies, preferably carcinomas, sarcomas and/or leukemias, particularly preferentially lung tumors, lymphomas, leukemias, sarcomas, mammary carcinomas and/or colon cancer.

With reference to further details regarding this aspect of the invention, reference can be made to the above explanations regarding the other aspects according to the invention, which apply analogously also with regard to this aspect of the invention.

Furthermore, another object of the present invention—according to a fifth aspect according to the invention—is the use of at least one locus-specific hybridization probe marked with at least two detection labels, together with at least one, particularly at least two, preferably at least three further locus-specific hybridization probes that are different from one another and each marked with at least a first detection label, for detection of chromosome abnormalities, particularly structural and/or numerical chromosome abnormalities, preferably structural chromosome abnormalities, by means of in situ hybridization, particularly by means of detection of chromosome regions and/or DNA regions in a biological sample, preferably in one or more cell(s) and/or in one or more cell nucleus/nuclei, preferably by means of a method as it was described above.

With regard to further details regarding this aspect of the invention, reference can be made to the above explanations regarding the other aspects according to the invention, which also apply analogously with regard to this aspect of the invention.

Finally, an object of the present invention—according to a sixth aspect according to the invention—is a kit or kit of parts or set for detection of chromosome abnormalities, particularly structural and/or numerical chromosome abnormalities, preferably structural chromosome abnormalities, by means of in situ hybridization, particularly by means of detection of chromosome regions and/or DNA regions in a biological sample, preferably in one or more cell(s) and/or in one or more cell nucleus/nuclei, comprising at least two, particularly at least three, preferably at least four locus-specific hybridization probes that are different from one another and each marked with a first detection label, wherein at least one of the locus-specific hybridization probes is marked with at least one further detection label, different from the first, with reference to the respective hybridization probe, particularly wherein the kit is intended and/or used for carrying out the method described above.

In this connection, it can particularly be provided that the at least two, particularly at least three, preferably at least four locus-specific hybridization probes that are different from one another are present in a common composition, particularly in a composition as it was described above.

Likewise, it can be provided that the at least two, particularly at least three, preferably at least four locus-specific hybridization probes that are different from one another are present in separate compositions, separate from one another.

With reference to further details regarding this aspect of the invention, reference can be made to the above explanations regarding the other aspects according to the invention, which apply analogously with regard to this aspect of the invention, as well.

BRIEF DESCRIPTION OF THE FIGURES

In the following, the present invention will be described in greater detail, using drawings and examples. The figures show:

FIG. 7: Schematic representation of a method according to the invention for detection of four numerical abnormalities and the signal pattern in the case of a) normal cells; or b) MET amplification.

FIG. 8: Schematic representation of a method according to the invention for detection of seven translocations or amplifications.

DETAILED DESCRIPTION OF THE FIGURES

Figure 1:
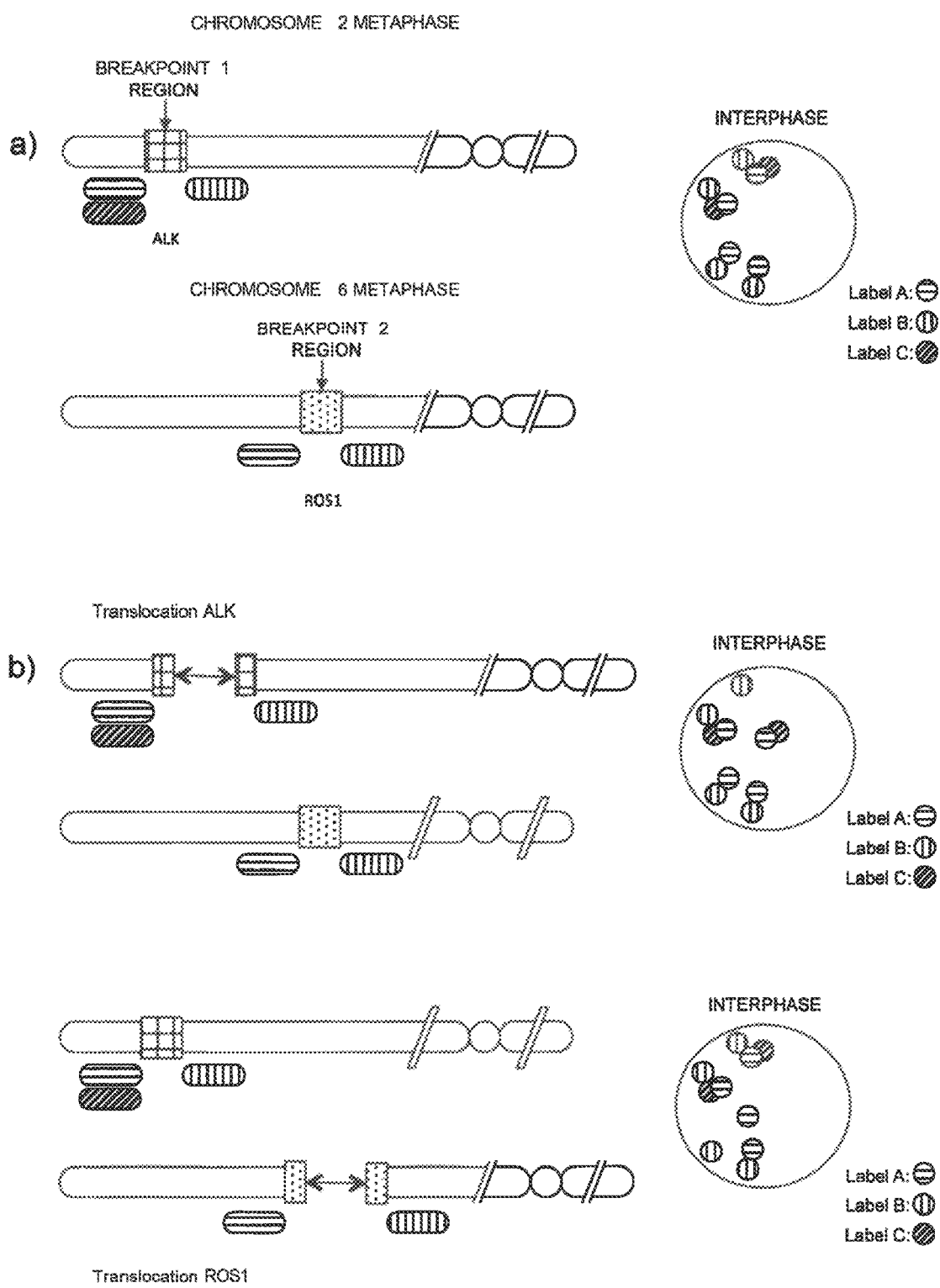
FIG. 1: Schematic representation of a method according to the invention for detection of two translocations, showing the signal pattern in the case of a) normal cells and b) cells with translocation of the ALK gene and the ROS1 gene.

FIG. 1 shows a schematic representation of a method according to the invention, for detection of two translocations, using four probes and three labels, wherein one probe is simultaneously marked with two labels. It shows the signal pattern in the case of normal cells, as well as in the case of cells with translocation of the ALK gene in 2p23 or of the ROS1 gene in 6q22.

The two breakpoint regions (ALK and ROS1) are each flanked by label A and B of the quadruple ISH probe, and result in a fusion signal A-B, in each instance. One side of the ALK breakpoint region is furthermore also flanked by label C, so that a mixed label A/C occurs.

In the interphase of a normal cell (without ALK or ROS1 abnormalities) the ROS1 gene loci are marked by fusion signals A-B, and ALK gene loci are marked by fusion signals A-B, which are accompanied by A/C mixed signals. In the interphase of a cell affected by an ALK translocation, the ALK gene affected by the translocation is marked by a separate signal of the label B as well as by a mixed signal NC that is separate from the former. In the interphase of a cell affected by an ROS1 translocation, the ROS1 gene affected by the translocation is marked by a separate signal of the label A, as well as by a separate signal of the label B.

Figure 2:
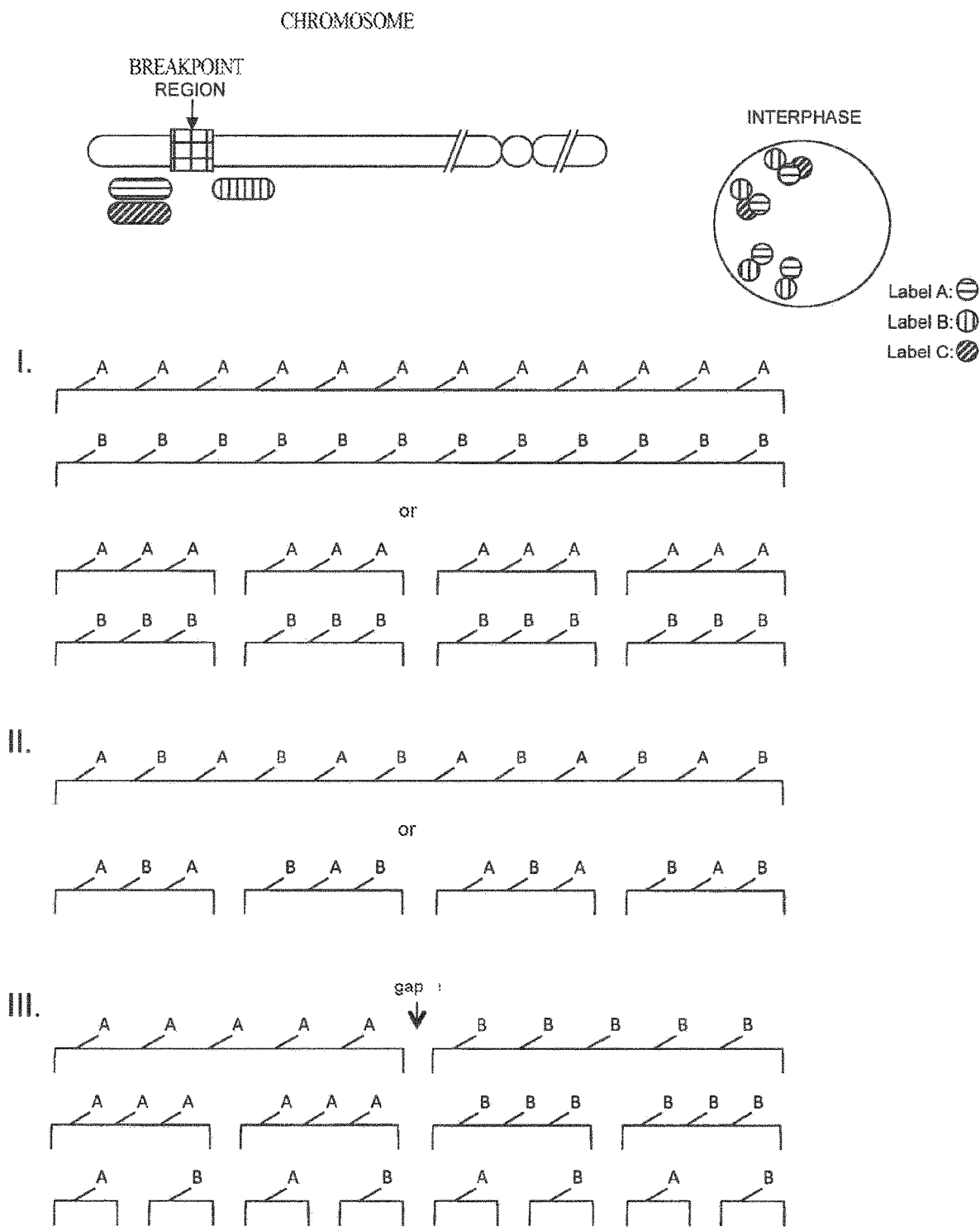
FIG. 2: Schematic representation of a method according to the invention, regarding the use of multiple labels for depiction of mixed labels and mixed signals.

FIG. 2 shows a schematic representation of a method according to the invention, relating to the use of multiple labels, for the representation of mixed labels and mixed signals. For the sake of clarity, only two labels are listed. Mixed signals that are specific for a locus-specific probes and therefore for a chromosomal region or a genomic segment can occur if I) fragments of a probe are each marked with different labels, and/or II) all the fragments of a probe, or, optionally, also only individual fragments of a probe are marked with multiple labels, and/or III) alternating fragments be marked with different labels, so that here, too, finally only a mixed signal is visible or detectable. In this regard, all or also only individual fragments according to I) torn) can be superimposed or can overlap (not shown), and mixed labels can also occur if individual fragments or fragment groups according to I) to III) have a spacing of up to 2 Mbp, for example in the "gap" that is shown.

Figure 3:
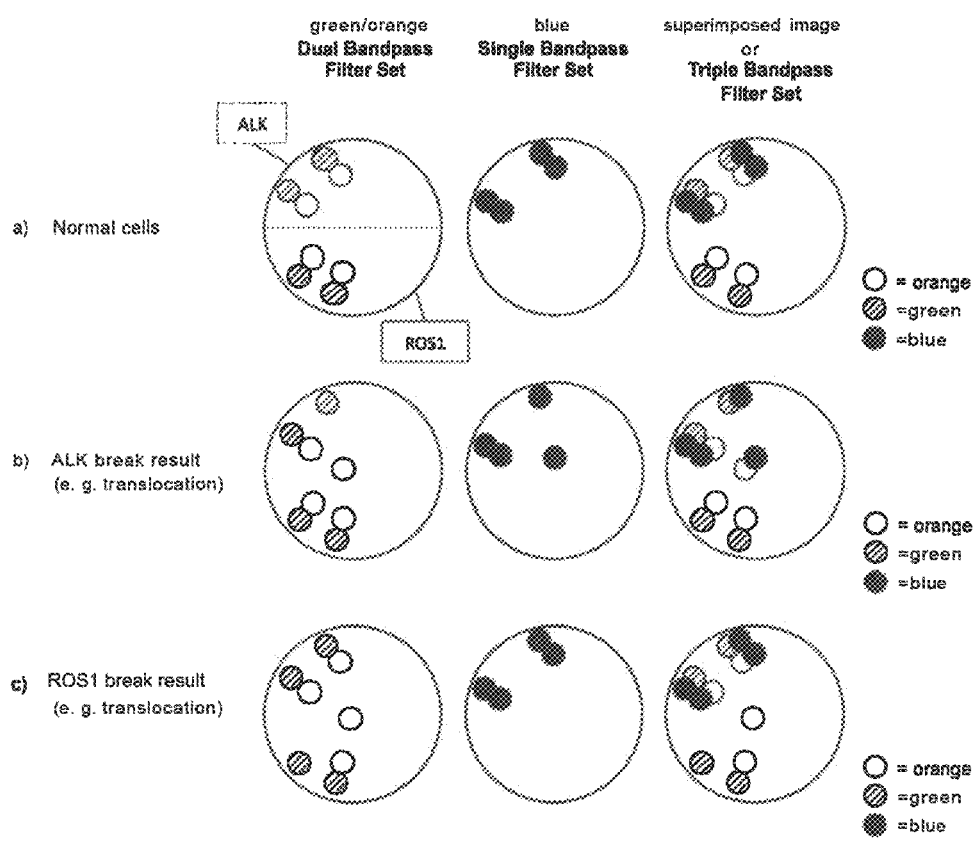
FIG. 3: Schematic of signal patterns when using a quadruple FISH probe "Zytolight SPEC ALK & ROS1 Break Apart Dual-Mix NG-FISH Probe" from the company ZytoVision GmbH with a) normal cells; b) an ALK translocation; and c) a ROS1 translocation.

FIG. 3 shows a schematic of signal patterns when using a corresponding quadruple FISH probe "Zytolight SPEC ALK & ROS1 Break Apart Dual-Mix NG-FISH Probe" from the company ZytoVision. The probe consists of green-marked polynucleotides (absorption at 503 nm and emission at 528 nm), which are directed, in 2p23, against sequences located proximal to the ALK breakpoint region, and, in 6q22, at sequences located proximal to the ROS1 breakpoint region, orange-marked polynucleotides (absorption at 547 nm and emission at 572 nm), which are directed, in 2p23, against sequences located distal to the ALK breakpoint region, and, in 6q22, against sequences located distal to the ROS1 breakpoint region, as well as blue-marked polynucleotides (absorption at 426 nm and emission at 480 nm), which are directed, in the region 2p23, against sequences located distal to and proximal to the ALK breakpoint region.

When suitable filter sets are used, the hybridization signals for the non-rearranged ALK gene appear as green-orange fluorescence fusion signals, which are composed of green/blue and orange/blue fluorescence mixed signals. The hybridization signals for the non-rearranged ROS1 gene appear as green-orange fluorescence fusion signals.

In the interphase of a normal cell (without ALK or ROS1 abnormalities), four green-orange fusion signals occur when using a suitable green-orange dual-bandpass filter set, two blue signals occur when using a suitable single-bandpass filter set and two green-orange fusion signals and two green-orange/blue fusion signals and mixed signals occur when using a suitable triple-bandpass filter set (cf. FIG. 3*a*).

A 2p23 locus affected by an ALK translocation is characterized by a separate green/blue mixed signal and a separate orange/blue mixed signal (cf. FIG. 3*b*).

A 6q22 locus affected by a ROS1 translocation is characterized by a separate green signal and a separate orange signal (cf. FIG. 3*c*).

When using suitable dual-bandpass filter sets for green and orange signals, green signals, as well as orange signals separate from them, therefore at first allow only the statement that fundamentally, an ALK or ROS1 translocation is present. A diagnostically possibly relevant distinction between ALK or ROS1 translocation can then take place with inclusion of the blue fluorescence signals. If the separate green signals blue signals (green/blue mixed signals) overlap, or if the separate orange signals blue signals (orange/blue mixed signals) overlap, this indicates an ALK translocation. If the separate green and orange signals do not overlap with blue signals, this indicates a ROS1 translocation.

Figure 4:
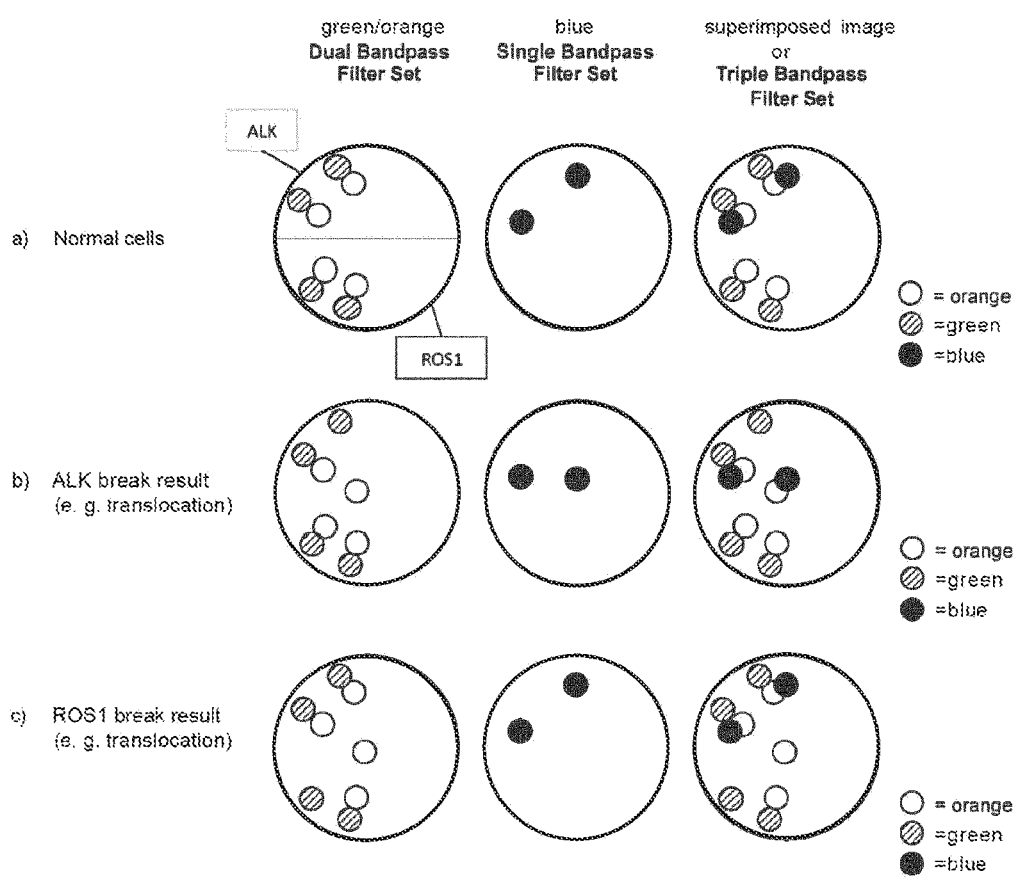
FIG. 4: Schematic of signal patterns when using a quadruple FISH probe "Zytolight SPEC ALK & ROS1 Break Apart single-Mix NG-FISH Probe" from the company ZytoVision GmbH with a) normal cells; b) an ALK translocation; and c) a ROS1 translocation.

FIG. 4 shows a schematic of signal patterns when using a corresponding quadruple FISH probe "Zytolight SPEC ALK & ROS1 Break Apart single-Mix NG-FISH Probe" from the company ZytoVision. The probe consists of green-marked polynucleotides (absorption at 503 nm and emission at 528 nm), which are directed, in 2p23, against sequences located proximal to the ALK breakpoint region, and, in 6q22, against sequences located proximal to the ROS1 breakpoint region, orange-marked polynucleotides (absorption at 547 nm and emission at 572 nm), which are directed, in 2p23, against sequences located distal to the ALK breakpoint region, and, in 6q22, against sequences located distal to the ROS1 breakpoint region, as well as blue-marked polynucleotides (absorption at 426 nm and emission at 480 nm), which are directed, in the region 2p23, against sequences located distal to the ALK breakpoint region.

When using suitable filters sets, the hybridization signals for the non-rearranged ALK gene appear as green-orange fluorescence fusion signals, which are composed of green and orange/blue fluorescence mixed signals. The hybridization signals for the non-rearranged ROS1 gene appear as green-orange fluorescence fusion signals.

In the interphase of a normal cell (without ALK or ROS1 abnormalities), four green-orange fusion signals appear when using a suitable green-orange dual-bandpass filter set, two blue signals appear when using a suitable single-bandpass filter set, and two green-orange fusion signals and two green-orange/blue fusion signals and mixed signals appear when using a suitable triple-bandpass filter set (cf. FIG. 4a).

A 2p23 locus affected by an ALK translocation is characterized by a separate green signal and a separate orange/blue mixed signal. (cf. FIG. 4b).

A 6q22 locus affected by a ROS1 translocation is characterized by a separate green signal and a separate orange signal (cf. FIG. 4c).

When using suitable dual-bandpass filter sets for green and orange signals, green signals, as well as orange signals separate from them, therefore at first only permit the statement that fundamentally, an ALK or ROS1 translocation is present. A diagnostically possibly relevant distinction between ALK or ROS1 translocation can then take place with inclusion of the blue fluorescence signals. If the separate orange signals blue signals (orange/blue mixed signals) overlap, this indicates an ALK translocation. If the separate orange signals do not overlap with blue signals, this indicates a ROS1 translocation.

Figure 5:
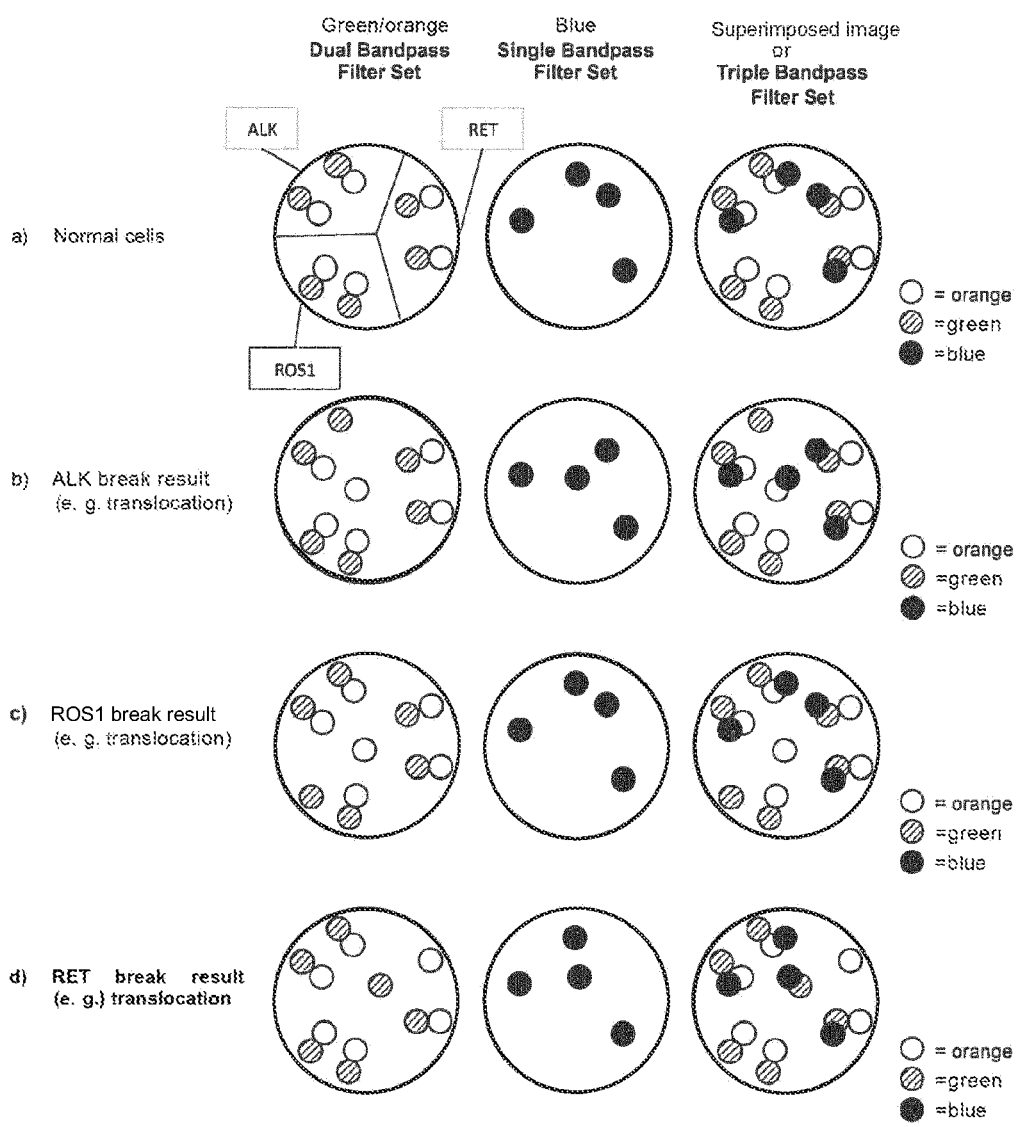
FIG. 5: Schematic of signal patterns when using a sextuple FISH probe "Zytolight SPEC ALK & ROS1 & RET Break Apart single-Mix NG-FISH Probe" from the company ZytoVision GmbH with a) normal cells; b) an ALK translocation; c) a ROS1 translocation; and d) a RET translocation.

FIG. 5 shows a schematic of signal patterns when using a corresponding sextuple FISH probe "Zytolight SPEC ALK & ROS1 & RET Break Apart Dual-Mix NG FISH Probe" from the company ZytoVision. The probe consists of green-marked polynucleotides (absorption at 503 nm and emission at 528 nm), which are directed, in 2p23, against sequences located proximal to the ALK breakpoint region, in 6q22, against sequences located proximal to the ROS1 breakpoint region, and, in 10q11, against sequences located proximal to the RET breakpoint region, orange-marked polynucleotides (absorption at 547 nm and emission at 572 nm), which are directed, in 2p23, against sequences located distal to the ALK breakpoint region, in 6q22, against sequences located distal to the ROS1 breakpoint region, and, in 10q11, against sequences located distal to the RET breakpoint region, as well as blue-marked polynucleotides (absorption at 426 nm and emission at 480 nm), which are directed, in region 2p23, against sequences located distal to the ALK breakpoint region, and, in 10q11, against sequences located proximal to the RET breakpoint region.

When using suitable filter sets, the hybridization signals for the non-rearranged ALK gene appear as green-orange fluorescence fusion signals, which are composed of green and orange/blue fluorescence mixed signals. The hybridization signals for the non-rearranged RET gene appear as green-orange fluorescence fusion signals, which are composed of green/blue mixed signals and orange signals. The hybridization signals for the non-rearranged ROS1 gene appear as green-orange fluorescence fusion signals.

In the interphase of a normal cell (without ALK, ROS1 or RET abnormalities), six green-orange fusion signals appear when using a suitable green-orange dual-bandpass filter set, four blue signals appear when using a suitable single-bandpass filter set, and two green-orange fusion signals, two green-orange/blue fusion signals and mixed signals and two green/blue-orange fusion signals and mixed signals appear when using a suitable triple-bandpass filter set (cf. FIG. 5a).

A 2p23 locus affected by an ALK translocation is characterized by a separate green signal and a separate orange/blue mixed signal (cf. FIG. 5b).

A 6q22 locus affected by a ROS1 translocation is characterized by a separate green signal and a separate orange signal (cf. FIG. 5c).

A 10q11 locus affected by a RET translocation is characterized by a separate orange signal and a separate green/blue mixed signal (cf. FIG. 5d).

In the case of use of suitable dual-bandpass filter sets for green and orange signals, green signals, and orange signals separate from them at first only permit the statement that fundamentally, an ALK, ROS1 or RET translocation is present. A diagnostically possibly relevant distinction between ALK, ROS1 or RET translocation can then take place with inclusion of the blue fluorescence signals. If the separate orange signals blue signals (orange/blue mixed signals) overlap, this indicates an ALK translocation. If the separate green signals blue signals (green/blue mixed signals) overlap, this indicates a RET translocation. If neither the separate orange signals nor the separate green signals overlap with blue signals, this indicates a ROS1 translocation.

Figure 6:
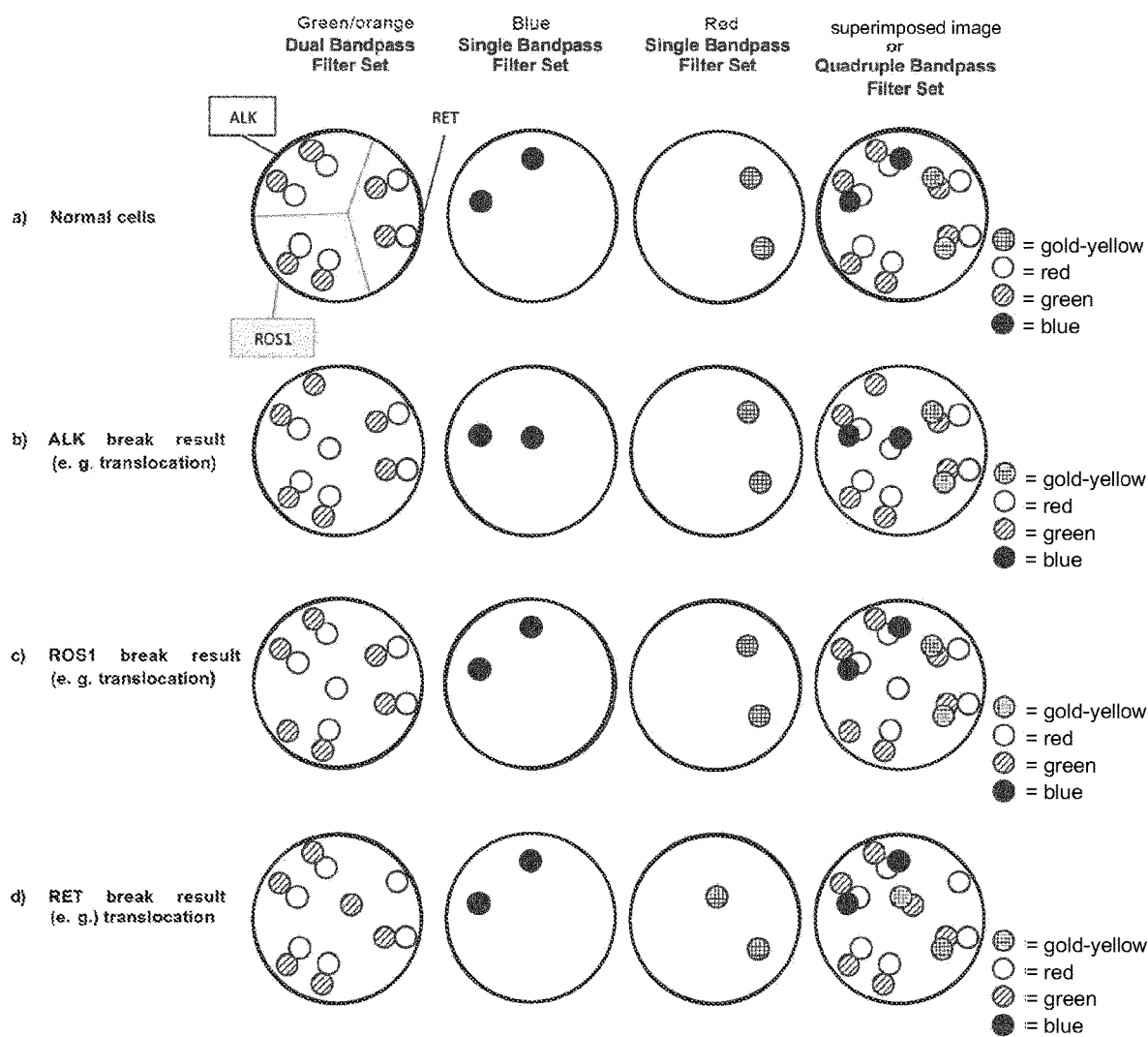
FIG. 6: Schematic of signal patterns when using a sextuple FISH probe "Zytolight SPEC ALK & ROS1 & RET Break Apart single-Mix II NG-FISH Probe" from the company ZytoVision GmbH with a) normal cells; b) an ALK translocation; c) a ROS1 translocation; and d) a RET translocation.

FIG. 6 shows a schematic of signal patterns when using a corresponding sextuple FISH probe "Zytolight SPEC ALK & ROS1 & RET Break Apart Dual-Mix II NG-FISH Probe" from the company ZytoVision GmbH. The probe consists of green-marked polynucleotides (absorption at 503 nm and emission at 528 nm), which are directed, in 2p23, against sequences located proximal to the ALK breakpoint region, in 6q22, against sequences located proximal to the ROS1 breakpoint region, and, in 10q11, against sequences located proximal to the RET breakpoint region, red-marked polynucleotides (absorption at 580 nm and emission at 599 nm), which are directed, in 2p23, against sequences located distal to the ALK breakpoint region, in 6q22, against sequences located distal to the ROS1 breakpoint region, and, in 10q11, against sequences located distal to the RET breakpoint region, blue-marked polynucleotides (absorption at 426 nm and emission at 480 nm), which are directed, in the region 2p23, against sequences located distal to the ALK breakpoint region, as well as gold-yellow-marked polynucleotides (absorption at 532 nm and emission at 553 nm), which are directed, in the region 10q11, against sequences located proximal to the RTE breakpoint region.

When using suitable filter sets, the hybridization signals for the non-rearranged ALK gene appear as green-red fluorescence fusion signals, which are composed of green and red/blue fluorescence mixed signals. The hybridization signals for the non-rearranged RET gene appear as green-red fluorescence fusion signals, which are composed of green/gold-yellow mixed signals and red signals. The hybridization signals for the non-rearranged ROS1 gene appear as green-red fluorescence fusion signals.

In the interphase of a normal cell (without ALK, ROS1 or RET abnormalities), six green-red fusion signals appear when using a suitable green-red dual-bandpass filter set, two blue signals appear when using a suitable single-bandpass filter set, and two gold-yellow signals appear when using a suitable single-bandpass filter set (cf. FIG. 6a).

A 2p23 locus affected by an ALK translocation is characterized by a separate green signal and a separate red/blue mixed signal (cf. FIG. 6b).

A 6q22 locus affected by a ROS1 translocation is characterized by a separate green signal and a separate red signal (cf. FIG. 6c).

A 10q11 locus affected by a RET translocation is characterized by a separate red signal and a separate green/gold-yellow mixed signal (cf. FIG. 6d).

When using suitable dual-bandpass filter sets for green and red signals, green signals, and red signals separate from them at first only permit the statement that fundamentally, an ALK, ROS1 or RET translocation is present. A diagnostically possibly relevant distinction between ALK, ROS1 or RET translocation can then take place with inclusion of the blue or gold-yellow fluorescence signals. If the separate red signals blue signals (red/blue mixed signals) overlap, this indicates an ALK translocation. If the separate green signals gold-yellow signals (green/gold-yellow mixed signals) overlap, this indicates a RET translocation. If neither the separate red signals nor the separate green signals overlap with blue or gold-yellow signals, this indicates a ROS1 translocation.

FIG. 7 shows a schematic representation of a method according to the invention for detection of four numerical abnormalities, using four probes and four labels, wherein three probes are simultaneously marked with two labels, in each instance, wherein the labels used for the combination differ from one another in the case of these three probes. It shows the signal pattern in the case of normal cells and in the case of cells with amplification of the MET gene in 7q31. The region 17q11.2-q12 of the ERBB2 gene is covered with the label A, the region 7p12 of the EGFR gene is covered with label A and furthermore label D, so that the mixed label ND comes about, the region 8p11.23-p11.22 of the FGFR1 gene is covered with label A and furthermore label C, so that a mixed label NC occurs, and the region 7q31 of the MET gene is covered with label A and furthermore label B, so that a mixed label NB comes about.

In the interphase of a normal cell (without a numerical ERBB2, EGFR, FGFR1 or MET abnormality), all the loci are marked by signals of the label A. Co-localization of a signal of label A with a signal of label B leads to a mixed label NB and marks the MET gene locus. Accordingly, the mixed label NC marks the FGFR1 gene locus, and the mixed label ND marks the EGFR gene locus. The ERBB2 gene locus is characterized in that no co-localization with another label comes about. In the interphase of a cell with MET gene amplification, an increase in signals of the label A, which co-localize with signals of the label B, comes about, and therefore an increase in signals of the mixed label NB comes about.

FIG. 8 shows a schematic representation of a method according to the invention for detection of seven translocations or amplifications, using 14 probes and five labels, in each instance, wherein a probe is simultaneously marked with two labels, and the amount ratio distinguishes the two labels per probe. The probes each flank a breakpoint region ("Breakpoint") or address an amplification region ("Amplification"), as well as a further region on the same chromosome (e.g. the centromere region), as shown in the left upper and right upper part of FIG. 8. The two probes of a chromosome are marked with two different labels and one same label (e.g. probe 1: 25% green, 75% blue and probe 2: 25% yellow and 75% blue). The two probes, which each flank a breakpoint region, therefore each produce fusion signals and mixed signals from three labels in a cell that is not affected by a translocation. The two probes, which each address an amplification region and a further region on the same chromosome, therefore each produce separate mixed signals in a cell that is not affected by an amplification (unless the distance between the two probes is so slight that fusion signals and mixed signals occur). Different mixed signals are generated by means of varying the amount ratio between the two labels with which a probe is marked, so that a plurality of probes can be marked in distinguishable manner, using the same labels (for example, in the example shown, four probes for the breakpoint regions 1 to 4: 25% to 75%; 50% to 50%; 75% to 25%, and 100% to 0%).

In the interphase of a normal cell (without translocations), the breakpoint regions of a gene are marked by mixed signals A-B and C-B, which combine to produce A/B/C fusion signals. In the interphase of a normal cell (without amplifications), the amplification regions of a gene are marked by the mixed signals A-B, and further regions on the same chromosome, for example centromere regions, are marked by the mixed signals C-B. In the interphase of a cell affected by a translocation, the gene affected by the translocation is marked by a separate signal of the label A-B and by a mixed signal C-B that is separate from the latter. In the interphase of a cell affected by an amplification, the gene affected by the amplification is marked by a reproduced mixed signal of a label pair, for example A-B.

Figure 9:
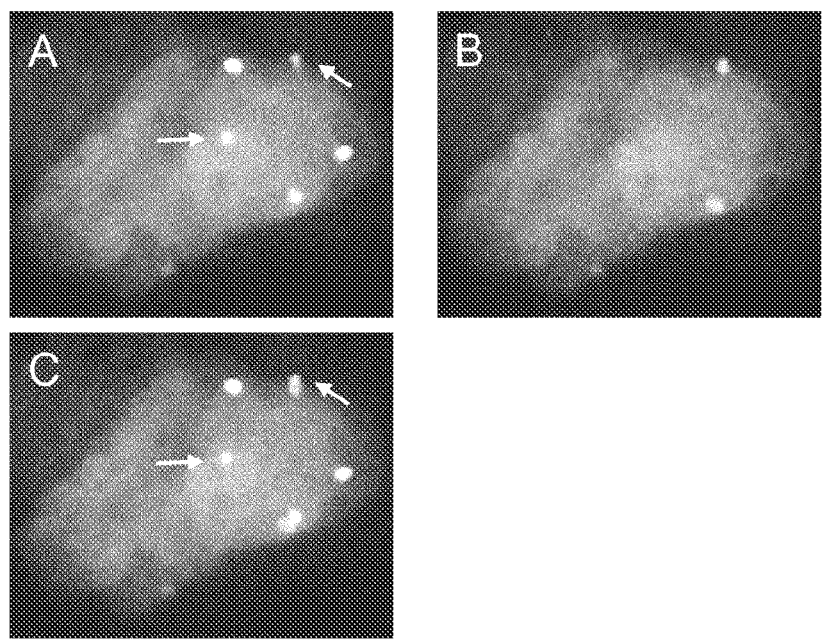
FIG. 9: FISH analysis for detection of a translocation of the ROS1 region in 6q22, using the quadruple FISH probe "Zytolight SPEC ALK & ROS1 Break Apart single-Mix NG-FISH Probe" from the company ZytoVision GmbH and the signal patterns A) for non-rearranged ALK gene; B) ROS1-specific green signals; and C) mixed signal confirming ROS1.

FIG. 9 shows a FISH analysis for detection of a translocation of the ROS1 region in 6q22, using the quadruple FISH-probe "Zytolight SPEC ALK & ROS1 Break Apart Single-Mix NG-FISH Probe" from the company ZytoVision. The probe consists of green-marked polynucleotides (absorption at 503 nm and emission at 528 nm), which are directed, in 2p23, against sequences located proximal to the ALK breakpoint region, and, in 6q22, against sequences located proximal to the ROS1 breakpoint region, orange-marked polynucleotides (absorption at 547 nm and emission at 572 nm), which are directed, in 2p23, against sequences located distal to the ALK breakpoint region, and, in 6q22, against sequences located distal to the ROS1 breakpoint region, as well as blue-marked polynucleotides (absorption at 426 nm and emission at 480 nm), which are directed, in the region 6q22, against sequences located proximal to the ROS1 breakpoint region.

When using suitable filter sets, the hybridization signals for non-rearranged ROS1 and/or ALK genes appear as green-orange fluorescence fusion signals, and, for a rearranged ROS1 and/or ALK genes, appear as a separate green signal and separate orange signal (see FIG. 9A, which shows the green and orange fluorescence signals). ROS1-specific green signals co-localize, in this regard, with blue fluorescence signals (see FIG. 9B, which shows the blue fluorescence signals), so that the non-rearranged ROS1 gene is composed of orange and green/blue fluorescence mixed signals. The hybridization signals for the non-rearranged ALK gene appear as green-orange fluorescence fusion signals, without mixed signals with blue fluorescence signals. The 6q22 locus affected by a ROS1 translocation is characterized by a separate green signal and a separate orange signal (arrows in FIGS. 9A and C). In this regard, the separate green signal overlaps with a blue signal. This green/blue mixed signal indicates ROS1, not ALK, as the gene affected by the translocation (see FIG. 9C, which shows the blue, green, and orange fluorescence signals). Using suitable filter sets, it is possible to make the signal pattern easily visible.

Figure 10:
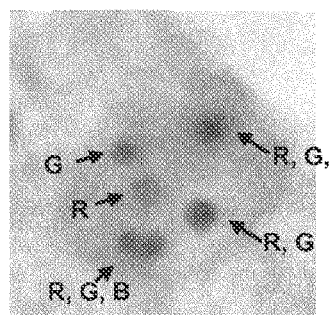
FIG. 10: CISH analysis for detection of a translocation of the ALK region in 2p23, using the quadruple CISH probe "ZytoDot SPEC ALK & ROS1 Break Apart single-MIX NG-FISH Probe" from the company ZytoVision GmbH.

FIG. 10 shows a CISH analysis for detection of a translocation of the ALK region in 2p23, using the quadruple CISH-probe "ZytoDot SPEC ALK & ROS1 Break Apart Single-MIX NG-FISH Probe" from the company ZytoVision. The probe consists of digoxigenin-marked polynucleotides, which are directed, in 2p23, against sequences located proximal to the ALK breakpoint region, and, in 6q22, against sequences located proximal to the ROS1 breakpoint region, DNP-marked polynucleotides, which are directed, in 2p23, against sequences located distal to the ALK breakpoint region, and, in 6q22, against sequences located distal to the ROS1 breakpoint region, as well as biotin-marked polynucleotides, which are directed, in the region 6q22, against sequences located distal to the ROS1 breakpoint region. Detection of the markings took place by way of primary (non-marked) antibodies (anti-DIG/anti-DNP/anti-BIO), which are detected by secondary polymerized enzyme-conjugated antibodies (HRP polymer/AP polymer/beta-GAL), as well as the enzymatic reaction of the substrates (AP-RED/HRP-GREEN/beta-GAL-BLUE), which leads to the formation of strong, permanent, red (R), green (G), and blue (B) signals, which can be depicted by light microscopy, for example, using a 40× dry lens.

Figure 11:
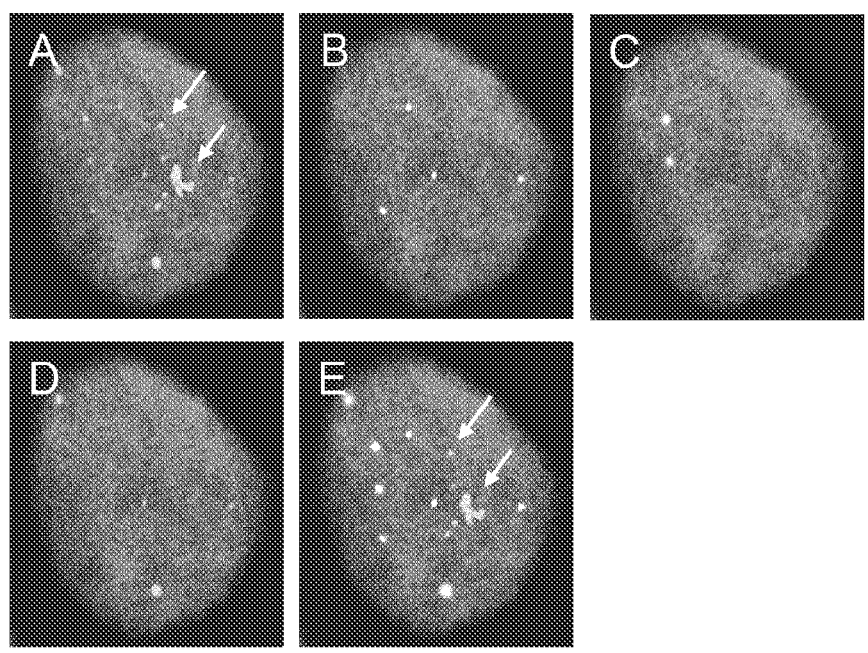
FIG. 11: FISH analysis for detection of the amplification of the ERBB2 region, using the quintuple probe "Zytolight SPEC ERBB2, EGFR, FGFR1, MET & SOX2 FiveCheck™ NG-FISH Probe" from the company ZytoVision and signal patterns for A) individual green signals; B) four blue signals; C) two gold-yellow signals; D) four red signals; and E) superimposed images of A-D.

FIG. 11 shows a FISH analysis for detection of the amplification of the ERBB2 region, using the quintuple FISH probe "Zytolight SPEC ERBB2, EGFR, FGFR1, MET & SOX2 FiveCheck™ NG-FISH Probe" from the company ZytoVision. The probe consists of green-marked polynucleotides (absorption at 503 nm and emission at 528 nm), which are directed against the region 17q11.2-q12 of the ERBB2 gene, the region 7p12 of the EGFR gene, the region 8p11.23-p11.22 of the FGFR1 gene, the region 7q31 of the MET gene, and the region 3q26.3-q27 of the SOX2 gene, as well as of blue-marked polynucleotides (absorption at 426 nm and emission at 480 nm), which are directed against the region of the EGFR gene and of the SOX2 gene, gold-yellow-marked polynucleotides (absorption at 532 nm and emission at 553 nm), which are directed against the region of the FGFR1 gene, and red-marked polynucleotides (absorption at 580 nm and emission at 599 nm), which are directed against the region of the MET gene and of the SOX2 gene.

When using suitable single-bandpass filter sets, it is possible to see nine individual green signals and a green signal cluster, which takes up the surface area of multiple individual green signals (see FIG. 11A), four blue signals (see FIG. 11B), two gold-yellow signals (see FIG. 11C), and four red signals (see FIG. 11D).

Superimposition of the images (see FIG. 11E) shows that a single green signal and the green signal cluster do not co-localize with signals of different colors (arrows). The single green signal is a non-amplified ERBB2 gene; the green signal cluster identifies an ERBB2 gene amplification. Co-localizing green/blue mixed signals identify two copies of the EGFR gene, co-localizing green/gold-yellow mixed signals identify two copies of the FGFR1 gene, co-localizing green/red mixed signals identify two copies of the MET gene, and co-localizing green/blue/red mixed signals identify two copies of the SOX2 gene (see FIG. 11E).

EXEMPLARY EMBODIMENTS

In order to document the properties of the method according to the invention further, the in situ hybridizations described below were furthermore carried out:

Example 1: FISH Analysis for Detection of Multiple Numerical Abnormalities in Different Cell Types, using the quintuple FISH probe "SPEC ERBB2, EGFR, FGFR1, MET & SOX2 FiveCheck™ NG-FISH Probe" from the company ZytoVision GmbH Carrying out the FISH took place on sections having a thickness of 3 to 5 μm, of formalin-fixed paraffin-embedded (FFPE) lung and mamma carcinoma preparations, without and with previously diagnosed ERBB2 gene amplification, which were applied to coated glass object carriers and baked at 58° C. overnight.

To remove the paraffin, the preparations were first heated on a hotplate for 10 minutes at 70° C. and subsequently incubated twice, for 10 minutes each time, at room temperature (RT), in 100% xylene.

Afterward, the preparations were rehydrated by means of a descending ethanol series (for 5 minutes at a time, at RT, in 96%, 96%, 90%, 70% denatured ethanol) and incubation in ultrapure water (twice each for two minutes at RT). For permeabilization of the cells, this is followed by heat pretreatment for 15 minutes at 98° C. in Heat Pretreatment Solution Citric (ZytoVision GmbH), followed by two further incubation steps for 2 minutes in ultrapure water at RT. The proteolytic pretreatment took place by means of dripping pepsin solution (Pepsin Solution, ZytoVision GmbH) onto the preparations and subsequent incubation in a humidity chamber at 37° C. for 25 minutes. After subsequent incubation for 5 min in Wash Buffer SSC (ZytoVision Gmb), the preparations were dehydrated (one minute, in each instance, RT in ultrapure water, 70%, 90%, 96% ethanol). After air drying of the preparations, 10 μl of the FISH probe Zytolight SPEC ERBB2, EGFR, FGFR1, MET & SOX2 FiveCheck™ NG-FISH Probe (ZytoVision GmbH) were applied to the sections directly, by means of a pipette.

The probe was a mixture on the basis of five locus-specific hybridization probes, wherein the mixture consisted of green-marked polynucleotides (absorption at 503 nm and emission at 528 nm), which were directed against the region 17q11.2-q12 of the ERBB2 gene, the region 7p12 of the EGFR gene, the region 8p11.23-p11.22 of the FGFR1 gene, the region 7q31 of the MET gene, and the region 3q26.3-q27 of the SOX2 gene, as well as of blue-marked polynucleotides (absorption at 426 nm and emission at 480 nm), which were directed against the region of the EGFR gene and of the SOX2 gene, gold-yellow-marked polynucleotides (absorption at 532 nm and emission at 553 nm), which were directed against the region of the FGFR1 gene, and red-marked polynucleotides (absorption at 580 nm and emission at 599 nm), which were directed against the region of the MET gene and of the SOX2 gene. Subsequently, glass covers were applied, free of air bubbles, and the edges were sealed with Fixogum (Marabu). After denaturing of the preparations for ten minutes at 75° C. on a hotplate, the hybridization was carried out in a preheated humidity chamber at 37° C., overnight (approximately 16 hours) in a heating oven.

After hybridization, the Fixogum was removed and the preparations were incubated for three minutes at 37° C. in wash buffer (1× Wash Buffer A, ZytoVision GmbH) in a glass cuvette. After removal of the glass covers, astringent washing for twice five minutes at 37° C. in wash buffer (1× Wash Buffer A, ZytoVision GmbH) took place. Subsequently, the preparations were dehydrated and dried in an ascending ethanol series, for one minute, in each instance, at RT in 70%, 90%, 96%), wherein the preparations were protected against direct light. After application of the counter-dye (20 μl DAPI DuraTect Solution (ZytoVision GmbH)), glass covers were applied, free of air bubbles, and the preparations were incubated for at least 30 minutes at RT, protected against light.

Subsequently, evaluation using the fluorescence microscope took place (Axio Scope.A1 with lighting unit HXP 120 V, Carl Zeiss Microscopy GmbH), using suitable filter sets (Sp. Green HC mFISH filter set; Sp. Red HC mFISH filter set; Sp. Aqua HC mFISH filter set; ZyGold HC mFISH filter set (all AHF Analysentechnik AG)).

In this connection, ten green signals were found in the cell nuclei, in each instance, in the preparations without ERBB2 amplification when using the green filters (or in the case of an ERBB2 amplification, more green signals, see FIG. 11A). Using the ZyGold filter, two gold-yellow signals were seen per cell nucleus, in each instance, the spatial position of which was identical with that of two green signals (as in FIG. 11C). Using the red filter, four red signals were seen per cell nucleus, in each instance, the spatial position of which was identical with that of four green signals (as in FIG. 11D). Using the aqua filter, four aqua signals were seen per cell nucleus, in each instance, the spatial position of which was identical with that of four green signals, as well as, in the case of two signals, in each instance, also identical with two red signals (as in FIG. 11D). It was possible to interpret the signal pattern as follows: Two green signals without spatially identical localization of signals of another color identified the two ERBB2 gene copies of a diploid cell. Two green signals with spatially identical localization of two aqua signals identified the two EGFR gene copies, two green signals with spatially identical localization of two gold-yellow signals identified the two FGFR1 gene copies, two green signals with spatially identical localization of two red signals identified the two MET gene copies, and two green signals with spatially identical localization of two red and two aqua signals identified the two SOX2 gene copies.

In the cell nuclei of the preparations with ERBB2 amplification, a signal pattern comparable to the one described above was found, with the exception that aside from nine green signals, a green signal cluster or signal pattern consisting of approximately fifteen signals lying so close together that they could not be separated was observed (cf. FIG. 11A). This green signal pattern did not co-localize with signals of a different color and therefore identified an ERBB2 gene amplification.

Example 2: FISH Analysis for Detection of Translocations of the ALK and ROS1 Regions in Different Cell Types, Using the Quadruple FISH Probe "Zytolight SPEC ALK & ROS1 Break Apart Single-Mix NG-FISH Probe" from the Company ZytoVision GmbH Carrying out the FISH took place using sections having a thickness of 3 to 5 µm, of formalin-fixed, paraffin-embedded (FFPE) cells of the cell lines Hela (ATCC® CCL-2™), HCC78 (made available by Prof. Schildhaus, Gottingen), and H3122 (made available by Prof. Schildhaus, Göttingen), which were applied to coated glass object carriers and baked overnight at 58° C.

For removal of the paraffin, the preparations were first heated on a hotplate for 10 min at 70° C. and subsequently incubated twice for 10 min each at room temperature (RT) in 100% xylene. Afterward, the preparations were rehydrated by means of a descending ethanol series, for five min, in each instance, at RT, in 96%, 96%, 90%, 70% denatured ethanol) and incubation in ultrapure water (twice two minutes at RT). For permeabilization of the cells, this was followed by heat pretreatment for 15 minutes at 98° C. in Heat Pretreatment Solution Citric (ZytoVision GmbH), followed by two further incubation steps for two minutes in ultrapure water at RT. The proteolytic pretreatment took place by means of dripping a pepsin solution (Pepsin Solution, ZytoVision GmbH) onto the preparations and subsequent incubation in a humidity chamber at 37° C. for 15 minutes. After subsequent incubation for five minutes in wash buffer (Wash Buffer SSC, ZytoVision GmbH), the preparations were dehydrated for one minute, in each instance, at RT in ultrapure water, 70%, 90%, 96% Ethanol). After air drying of the preparations, 10 µl of the FISH probe Zytolight SPEC ALK & ROS1 Break Apart Single-Mix NG-FISH Probe (ZytoVision GmbH), in each instance, were applied to the sections directly by means of a pipette.

The probe was a mixture on the basis of four locus-specific hybridization probes, wherein the mixture consisted of green-marked polynucleotides (absorption at 503 nm and emission at 528 nm), which were directed, in 2p23, against sequences located proximal to the ALK breakpoint region, and, in 6q22, against sequences located proximal to the ROS1 breakpoint region, orange-marked polynucleotides (absorption at 547 nm and emission at 572 nm), which were directed, in 2p23, against sequences located distal to the ALK breakpoint region, and, in 6q22, against sequences located distal to the ROS1 breakpoint region, as well as blue-marked polynucleotides (absorption at 426 nm and emission at 480 nm), which were directed, in the region 6q22, against sequences located proximal to the ROS1 breakpoint region. Subsequently, glass covers were applied, free of air bubbles, and the edges were sealed with Fixogum (Marabu). After denaturing of the preparations over a period of 10 minutes at 75° C. on a hotplate, the hybridization was carried out in a preheated humidity chamber at 37° C. overnight (approx. 16 hours) in a heating oven.

After hybridization, the Fixogum was removed and the preparations were incubated for three minutes at 37° C. in wash buffer (lx Wash Buffer A, ZytoVision GmbH) in a glass cuvette.

After removal of the glass covers, twice astringent washing took place for five minutes each at 37° C. in wash buffer (1× Wash Buffer A, ZytoVision GmbH). Subsequently, the preparations were dehydrated in an ascending ethanol series (for one minute, in each instance, at RT in 70%, 90%, 96% ethanol) and air-dried, wherein the samples were protected against direct light incidence. After application of the counter-dye (20 µl DAPI DuraTect Solution, ZytoVision GmbH), glass covers were applied, free of air bubbles, and the preparations were incubated for at least 30 minutes at RT, protected against light.

Subsequently, evaluation using the fluorescence microscope took place (Axio Scope.A1 with lighting unit HXP 120 V, Carl Zeiss Microscopy GmbH), using suitable filter sets (Dualband Green/Orange-Red filter set, AHF Analysentechnik; Sp. Aqua HC mFISH filter set, AHF Analysentechnik).

In this regard, when using the orange/green double filter, six orange/green fusion signals were found in the cell nuclei of the HeLa cell line, in the majority of the analyzed nuclei, in each instance; no individual green and/or orange signals were seen. Using the aqua filter, three aqua signals were seen, in each instance, per cell nucleus, the spatial position of which was identical with that of the fusion signals. The signal pattern was interpreted, in agreement with the literature, as three copies of the ALK gene and three copies of the ROS1 gene. No ALK or ROS1 translocations were present.

In the cell nuclei of the cell line H3122, for which a translocation of the ALK gene is described in the literature, seven orange/green fusion signals and a single orange signal were found, in each instance, when using the orange/green double filter, in the majority of the analyzed nuclei. When using the aqua filter, two aqua signals were seen per cell nucleus, in each instance, the spatial position of which was identical with that of two of the fusion signals. The signal pattern was interpreted, in agreement with the literature, as six copies of the ALK gene, one of them affected by a translocation, and two copies of the ROS1 gene.

In the cell nuclei of the cell line HCC78, for which a translocation of the ROS1 gene is described in the literature, four orange/green fusion signals, in each instance, two individual orange signals, and two individual green signals, i.e. separate from the others, were found when using the orange/green double filter, in the majority of the analyzed nuclei. When using the aqua filter, four aqua signals were seen per cell nucleus, in each instance, the spatial position of which was identical with two of the fusion signals and the two separate green signals. The signal pattern was interpreted, in agreement with the literature, as four copies of the ROS1 gene, wherein two of them were affected by a translocation, and two copies of the ALK gene.

Example 3: FISH Analysis for Detection of a Translocation of the ROS1-Region in 6q22, Using the Quadruple FISH Probe "Zytolight SPEC ALK & ROS1 Break Apart Single-Mix NG-FISH Probe" from the Company ZytoVision GmbH A FISH analysis for detection of a translocation of the ROS1-Region in 6q22 was carried out using the quadruple FISH probe "Zytolight SPEC ALK & ROS1 Break Apart Single-Mix NG-FISH Probe" from the company ZytoVision GmbH. The probe was a mixture on the basis of four locus-specific hybridization probes, wherein the mixture consisted of green-marked polynucleotides (absorption at 503 nm and emission at 528 nm), which were directed, in 2p23, against sequences located proximal to the ALK breakpoint region, and, in 6q22, against sequences located proximal to the ROS1 breakpoint region, orange-marked polynucleotides (absorption at 547 nm and emission at 572 nm), which were directed, in 2p23, against sequences located distal to the ALK breakpoint region, and, in 6q22, against sequences located distal to the ROS1 breakpoint region, as well as blue-marked polynucleotides (absorption at 426 nm and emission at 480 nm), which were directed, in the region 6q22, against sequences located proximal to the ROS1 breakpoint region.

When using suitable filter sets, the hybridization signals for non-rearranged ROS1 and/or ALK genes appear as green-orange fluorescence fusion signals, and, for a rearranged ROS1 and/or ALK gene, as a separate green and separate orange signal. ROS1-specific green signals co-localized, in this regard, with blue fluorescence signals, so that the non-rearranged ROS1 gene was composed of orange and green/blue fluorescence mixed signals. The hybridization signals for the non-rearranged ALK gene appeared as green-orange fluorescence fusion signals without mixed signals with blue fluorescence signals (FIG. 9A). The 6q22 locus affected by a ROS1 translocation was characterized by a separate green signal and a separate orange signal (FIG. 9A arrows).

In this regard, the separate green signal overlapped with a blue signal (blue signals FIG. 9B). This green/blue mixed signal indicated ROS1, not ALK, as the gene affected by the translocation. It was possible to make the signal pattern easily visible, using suitable filter sets.

Example 4: CISH Analysis for Detection of a Translocation of the ALK Region in 2p23, Using the Quadruple CISH Probe "ZytoDot SPEC ALK & ROS1 Break Apart Single-MIX NG-FISH Probe" from the Company ZytoVision GmbH Furthermore, a CISH analysis for detection of a translocation of the ALK-Region in 2p23 was carried out, using the quadruple CISH probe "ZytoDot SPEC ALK & ROS1 Break Apart Single-MIX NG-FISH Probe" from the company ZytoVision GmbH. The probe was a mixture on the basis of four locus-specific hybridization probes, wherein the mixture consisted of digoxigenin-marked polynucleotides, which were directed, in 2p23, against sequences located proximal to the ALK breakpoint region, and, in 6q22, against sequences located proximal to the ROS1 breakpoint region, DNP-marked polynucleotides, which were directed, in 2p23, against sequences located distal to the ALK breakpoint region, and, in 6q22, against sequences located distal to the ROS1 breakpoint region, as well as biotin-marked polynucleotides, which were directed, in the region 6q22, against sequences located distal to the ROS1 breakpoint region. Detection of the markings took place by way of primary (non-marked) antibodies (Anti-DIG/Anti-DNP/Anti-BIO), which were detected by secondary polymerized enzyme-conjugated antibodies (HRP-polymer/AP-polymer/beta-GAL), as well as enzymatic reaction of the substrates (AP-RED/HRP-GREEN/beta-GAL-BLUE), which led to the formation of strong, permanent, red, green, and blue signals, which it was possible to depict using light microscopy, for example with a 40× dry lens.

Diploid or disomic cell nuclei without rearrangements or translocations of the ALK or ROS1 gene showed two signals, each consisting of a red signal and a green signal, which lay so close together that they could not be separated or partially overlapped or mixed, and were specific for the two copies of the ALK gene (FIG. 10). Furthermore, two signals were found, which each consisted of a red signal, a green signal, and a blue signal, in each instance, and lay so close together that they could not be separated or partially overlapped or mixed, and were specific for the two copies of the ROS1 gene.

Diploid or disomic cell nuclei with rearrangements or translocations of an ALK gene, but not of the ROS1 allele, showed a red-green signal, which was specific for the non-rearranged ALK allele (FIG. 10). Furthermore, they showed a single green signal and a single red signal, separate from the former, which was specific for a rearranged ALK allele (FIG. 10, arrows "G"=green and "R"=red). Furthermore, two red-green-blue signals were found, which were specific for the two copies of the ROS1 gene.

Diploid or disomic cell nuclei with rearrangements or translocations of a ROS1 gene, but not the ALK allele, showed a red-green-blue signal, which was specific for the non-rearranged ROS1 allele. Furthermore, they showed a single green signal and a single red-blue signal, separate from the former, for a rearranged ROS1 allele, as well as two red-green signals, which were specific for the two copies of the ALK gene.

Example 5: FISH Analysis for Detection of the Amplification of the ERBB2 Region, Using the Quintuple FISH Probe "Zytolight SPEC ERBB2, EGFR, FGFR1, MET & SOX2 FiveCheck™ NG-FISH Probe" from the Company ZytoVision Finally, a FISH analysis for detection of the amplification of the ERBB2 region was carried out, using the quintuple FISH probe "Zytolight SPEC ERBB2, EGFR, FGFR1, MET & SOX2 FiveCheck™ NG-FISH Probe" from the company ZytoVision. The probe was a mixture on the basis of five locus-specific hybridization probes, wherein the mixture consisted of green-marked polynucleotides (absorption at 503 nm and emission at 528 nm), which were directed against the region 17q11.2-q12 of the ERBB2 gene, the region 7p12 of the EGFR gene, the region 8p11.23-p11.22 of the FGFR1 gene, the region 7q31 of the MET gene, and the region 3q26.3-q27 of the SOX2 gene, as well as of blue-marked polynucleotides (absorption at 426 nm and emission at 480 nm), which were directed against the region of the EGFR gene and of the SOX2 gene, gold-yellow-marked polynucleotides (absorption at 532 nm and emission at 553 nm), which were directed against the region of the FGFR1 gene, and red-marked polynucleotides (absorption at 580 nm and emission at 599 nm), which were directed against the region of the MET gene and of the SOX2 gene.

When using suitable single-bandpass filter sets, nine individual green signals and one green signal cluster, which took up the surface area of multiple individual green signals, were found, along with four blue signals, two gold-yellow signals, and four red signals.

Superimposition of the images shows that a single green signal as well as the green signal cluster did not co-localize with signals of other colors. The single green signal involved a non-amplified ERBB2 gene; the green signal cluster identified an ERBB2 gene amplification. Co-localizing green/blue mixed signals identified two copies of the EGFR genes, co-localizing green/gold-yellow mixed signals identified two copies of the FGFR1 gene, co-localizing green/red mixed signals identified two copies of the MET gene, and co-localizing green/blue/red mixed signals identified two copies of the SOX2 gene.

FURTHER ASPECTS OF THE PRESENT INVENTION $1^{st}$ aspect: According to a first aspect, the present invention relates to a method for detection of multiple different chromosome regions or DNA regions in a cell, for detection (and for differentiation) of (multiple) structural and/or numerical chromosome abnormalities, based on directly or indirectly marked nucleic acid fragments (probes), characterized in that 4 to 24 locus-specific probes are each marked with one of 1 to 24 different labels, and that at least one locus-specific probe is simultaneously also marked with at least one further label (and maximally six further labels), so that mixed signals occur by way of these mixed labels, wherein optionally, individual probes with the same mixed labels can be differentiated on the basis of different ratios of the individual labels, by means of different mixed signals that can result from them, so that abnormal signal patterns in the case of a chromosome abnormality can be clearly assigned to an affected locus, i.e. the locus affected by an abnormality can be identified using the mixed signal pattern, wherein mixed signals can occur if all the fragments or optionally also only individual fragments of a probe a) are marked with multiple labels and/or b) the same fragments are marked with different labels and/or c) alternating fragments are marked with different labels, wherein the aforementioned fragments can also be superimposed or can also have distances of up to 2 Mbp in a genomic region.

$2^{nd}$ aspect: According to a further aspect, the present invention relates to a method according to the first aspect, wherein at least two, optionally three, optionally four, optionally five, optionally six, optionally seven, optionally eight, optionally nine, and optionally ten locus-specific probes are simultaneously marked with at least one further label and maximally six further labels, so that mixed signals occur by way of these mixed labels.

$3^{rd}$ aspect: According to a further aspect, the present invention relates to a method according to the first aspect, wherein at least 5 to 24, optionally 6 to 24, optionally 7 to 24 and optionally 8 to 24 locus-specific probes are each marked with one of 1 to 24 different labels.

$4^{th}$ aspect: According to a further aspect, the present invention relates to a method for the detection of multiple different chromosome regions or DNA regions in a cell, for detection of structural chromosome abnormalities, based on directly or indirectly marked nucleic acid fragments (probes), characterized in that a first probe (probe 1) marked with a label A and a second probe (probe 2) marked with a label B flank a breakpoint region 1, which probes form the fusion signals A-B, and, according to the same principle, 2 to 12 further probes (probes 3 to 14) flank 1 to 6 further breakpoint regions (breakpoint regions 2-7), and also form the fusion signals A-B, in each instance, and further probes, but at least one of the aforementioned probes are simultaneously marked also with further labels, particularly selected from the labels C to F, or optionally in different ratios of these labels to one another, and thereby form specific fusion signals and mixed signals A-B/X, wherein a) X label C and/or label D and/or label E and/or label F can be in different ratios, in each instance, and b) the specific fusion signals and mixed signals A-B/X change at a chromosome abnormality to form new, separate mixed signals A/X or B/X, and c) optionally, in addition, specific fusion signals change to new separate signals A or B (if no further label X is used for a probe pair) and d) on the basis of these changed signal patterns, the affected breakpoint region can be clearly detected.

5th aspect: According to a further aspect, the present invention relates to a method for the detection of multiple different chromosome regions or DNA regions in a cell, for the detection of structural chromosome abnormalities, based on directly or indirectly marked nucleic acid fragments (probes), characterized in that a first probe (probe 1) marked with a label A and a second probe (probe 2) marked with a label B flank a breakpoint region 1, which probes form fusion signals A-B, and a third probe (probe 3) marked with a label A and a fourth probe (probe 4) marked with a label B flank a breakpoint region 2, also form the fusion signals A-B, and the probes 3 and/or 4 simultaneously are also marked with a further label C, and thereby form the fusion signals A-B/C, wherein the aforementioned signals change at a chromosome abnormality, to form separate signals A and/or B (breakpoint 1) or fusion signals A/C and/or B/C (breakpoint 2).

$6^{th}$ aspect: According to a further aspect, the present invention relates to a method according to one of the aforementioned aspects, wherein at first, only the signals A and/or B are considered, on the basis of the use of suitable filters, using the label A and/or label B, and only if abnormal signal patterns of A and/or B are present, the further labels C to F are considered for a clear determination of the affected chromosomal region.

$7^{th}$ aspect: According to a further aspect, the present invention relates to a method according to one of the aforementioned aspects, wherein the genomic regions detected by means of the locus-specific probes are smaller than 5 Mbp, optionally smaller than 2 Mbp, optionally smaller than 1 Mbp, optionally smaller than 750 kb, optionally smaller than 500 kb, optionally smaller than 250 kb, optionally smaller than 100 kb, optionally smaller than 10 kb, and optionally smaller than 1 kb.

$8^{th}$ aspect: According to a further aspect, the present invention relates to a method according to one of the aforementioned aspects, wherein instead of mixed labels of a probe, multiple ones of the same probes with different labels are used, wherein optionally, the same probes are viewed as being the same even if they agree by at least 90%, optionally at least 80%, optionally at least 70%, optionally at least 60%, and optionally at least 50%.

9$^{th}$ aspect: According to a further aspect, the present invention relates to a method according to one of the aforementioned aspects, wherein preferentially, chromosome abnormalities can be detected in malignancies, preferentially in carcinomas, preferentially in sarcomas, and preferentially in leukemias.

10$^{th}$ aspect: According to a further aspect, the present invention relates to a method according to one of the aforementioned aspects, wherein the probes are polynucleotides, modified polynucleotides or modified nucleic acid fragments or oligonucleotides or modified oligonucleotides.

11$^{th}$ aspect: According to a further aspect, the present invention relates to a method according to one of the aforementioned aspects, wherein the label is selected from the group comprising dyes, dye substrates, chemiluminescence dyes (e.g. acridinium), radioisotopes, Spin labels, enzymes (e.g. alkaline phosphatase, horseradish peroxidase, soybean peroxidase and/or beta-galactosidase), haptens (e.g. digoxigenin, biotin, 5(6)-carboxyfluorescein, rhodamine, bromine deoxyuridine, acetylaminofluorene, trinitrophenol, trinitrophenol derivative, estradiol, and/or DNP), Quantum Dots, Beads, amino hexyls, pyrenes and fluorescence dyes (e.g. fluorescein, fluorescein derivative, 5(6)-carboxyfluorescein, coumarin, coumarin derivative, rhodamine, rhodamine derivative, tetramethyl rhodamine, lissamine, Texas Red, AMCA, TRITC, IR dye, Alexa dye, Dyomics dye, phycoerythrins, Cascade Blue, Oregon Green 488, Pacific Blue and/or Rhodamine Green).

12$^{th}$ aspect: According to a further aspect, the present invention relates to a method according to one of the aforementioned aspects, wherein the method is carried out by means of the FISH method, using directly built-in fluorescence dyes for the entire visible, infrared and ultraviolet emissions region and preferentially for the emissions regions green, orange/red, red, gold, and blue.

13$^{th}$ aspect: According to a further aspect, the present invention relates to a method according to one of the aforementioned aspects, wherein the method is carried out by means of the BrISH method, using biotin, digoxigenin and DNP, which combine with antibody-coupled alkaline phosphatase, antibody-coupled peroxidase, and antibody-coupled beta-galactosidase.

14$^{th}$ aspect: According to a further aspect, the present invention relates to a method according to one of the aforementioned aspects, wherein the genes ALK, ROS1, RET, NRG1, NTRK1, CARS, EML4, FGFR2, FGFR3, KIF5B, TGF, BCR, ABL, ALK, BCL2, BCL6, BIRC3, CCND1, EGR1, ETV6, FGFR1, FGFR3, IGH, KMT2A, MYC, PML, RARA, RUNX1, RUNX1T1, EWSR1, CHOP, FUS, COL1A1, DDIT3, JAZF1, NR4A3, FOXO1, FUS, PAX3, PAX7, PDGFB, SS18, TFE3, USP6, WT1, HER2/ERBB2, FGFR1, ALK, CCND1, CDK4, CD274, PDCD1LG2, EGR1, EGFR, ESR1, ETV1, FGF3,4,19, FGFR2, FGFR3, FHIT (RCC), KRAS, MDM2, MDM4, MET, MYB, MYC, MYCN, PIK3CA, PTEN, SMARCB1, SOX2, TERT, TOP2A, TP53, TYMS and/or VHL are examined for chromosome abnormalities.

15$^{th}$ aspect: According to a further aspect, the present invention relates to a formulation for the detection of multiple different chromosome regions or DNA regions in a cell, for detection and differentiation of preferably multiple structural and/or numerical chromosome abnormalities, based on directly or indirectly marked nucleic acid fragments (probes), wherein 4 to 24 locus-specific probes are each marked with one of from 1 to 24 different labels, and wherein at least one locus-specific probe is simultaneously marked also with at least one further label and maximally 6 further labels, so that mixed signals occur by means of these mixed labels, wherein optionally, single probes with the same mixed labels can be differentiated on the basis of different ratios of the individual labels, by means of the resulting different mixed signals, so that abnormal signal patterns in the case of a chromosome abnormality can be clearly assigned to an affected locus and/or so that the locus affected by an abnormality can be identified using the mixed signal pattern, wherein mixed signals can occur if all the fragments or optionally also only individual fragments of a probe a) are marked with multiple labels and/or b) the same fragments are marked with different labels and/or c) alternately, fragments are marked with different labels, wherein the aforementioned fragments can also be superimposed or also have distances of up to 2 Mb in a genomic region.

16t$^{h}$ aspect: According to a further aspect, the present invention relates to a preparation according to the 15$^{th}$ aspect, wherein the probes are configured in accordance with aspects 1 to 13.

The invention claimed is:

1. A composition for detection of at least two chromosome abnormalities that are different from one another by in situ hybridization, wherein the composition comprises at least four locus-specific hybridization probes that are different from one another, wherein said at least four locus-specific hybridization probes comprise:

(a) a first probe pair comprising a first locus-specific hybridization probe marked with a detection label A and a second locus-specific hybridization probe marked with a detection label B, wherein said first probe pair is configured to hybridize with nucleic acid sequences flanking a first chromosome segment proximally and distally, such that an end of the first locus-specific hybridization probe hybridizes with a first base that has a distance of 0 to 1 Mbp proximal to the first chromosome segment, and an end of the second locus-specific hybridization probe hybridizes with a second base that has a distance of 0 to 1 Mbp distal from the first chromosome segment, thereby flanking the first chromosome segment and generating a fusion signal A-B in a signal pattern generated by in situ hybridization, and (b) a second probe pair comprising a third locus-specific hybridization probe marked with the detection label A and a fourth locus-specific hybridization probe marked with the detection label B, wherein said second probe pair is configured to hybridize with nucleic acid sequences flanking a second chromosome segment proximally and distally, such that an end of the third locus-specific hybridization probe hybridizes with a third base that has a distance of 0 to 1 Mbp proximal to the second chromosome segment, and an end of the fourth locus-specific hybridization probe hybridizes with a fourth base that has a distance of 0 to 1 Mbp distal from the second chromosome segment, and generates a fusion signal A-B in a signal pattern generated by in situ hybridization, and wherein the third locus-specific hybridization probe and/or the fourth locus-specific hybridization probe in the second probe pair is/are marked with a further detection label $X_1$, thereby flanking the second chromosome segment and generating fusion signals and mixed signals A-BX$_1$ and/or AX$_1$-B in a signal pattern generated by in situ hybridization; and wherein the hybridization probes are labeled directly with the detection labels.

2. A kit for detection of at least two chromosome abnormalities that are different from one another by in situ hybridization, comprising at least four locus-specific hybridization probes that are different from one another, wherein said at least four locus-specific hybridization probes comprise:

(a) a first probe pair comprising a first locus-specific hybridization probe marked with a detection label A and a second locus-specific hybridization probe marked with a detection label B, wherein said first probe pair is configured to hybridize with nucleic acid sequences flanking a first chromosome segment proximally and distally, such that an end of the first locus-specific hybridization probe hybridizes with a first base that has a distance of 0 to 1 Mbp proximal to the first chromosome segment, and an end of the second locus-specific hybridization probe hybridizes with a second base that has a distance of 0 to 1 Mbp distal from the first chromosome segment, thereby flanking the first chromosome segment and generating a fusion signal A-B in a signal pattern generated by in situ hybridization, and (b) a second probe pair comprising a third locus-specific hybridization probe marked with the detection label A and a fourth locus-specific hybridization probe marked with the detection label B, wherein said second probe pair is configured to hybridize with nucleic acid sequences flanking a second chromosome segment proximally and distally, such that an end of the third locus-specific hybridization probe that comes closest to the second chromosome hybridizes with a third base that has a distance of 0 to 1 Mbp proximal to the second chromosome segment, and an end of the fourth locus-specific hybridization probe hybridizes with a fourth base that has a distance of 0 to 1 Mbp distal from the second chromosome segment, and generates a fusion signal A-B in a signal pattern generated by in situ hybridization, and wherein the third locus-specific hybridization probe and/or the fourth locus-specific hybridization probe in the second probe pair is/are marked with a further detection label X$_1$, thereby flanking the second chromosome segment and generates fusion signals and mixed signals A-BX$_1$ and/or AX$_1$-B in a signal pattern generated by in situ hybridization; and wherein the hybridization probes are labeled directly with the detection labels.

3. The kit according to claim 2, wherein the at least four locus-specific hybridization probes that are different from one another are present in a common composition.

4. A composition for use in diagnosis and/or prognosis of illnesses that are connected with chromosome abnormalities, wherein the illnesses are selected from the group consisting of carcinomas, sarcomas and/or leukemias, wherein the composition comprises at least four locus-specific hybriization probes that are different from one another, wherein said at least four locus-specific hybridization probes comprise:

(a) a first probe pair comprising a first locus-specific hybridization probe marked with a detection label A and a second locus-specific hybridization probe marked with a detection label B, wherein said first probe pair is configured to hybridize with nucleic acid sequences flanking a first chromosome segment proximally and distally, such that an end of the first locus-specific hybridization probe hybridizes with a first base that has a distance of 0 to 1 Mbp proximal to the first chromosome segment, and an end of the second locus-specific hybridization probe hybridizes with a second base that has a distance of 0 to 1 Mbp distal from the first chromosome segment, thereby flanking the first chromosome segment and generating a fusion signal A-B in a signal pattern generated by in situ hybridization, and (b) a second probe pair comprising a third locus-specific hybridization probe marked with the detection label A and a fourth locus-specific hybridization probe marked with the detection label B, wherein said second probe pair is configured to hybridize with nucleic acid sequences flanking a second chromosome segment proximally and distally, such that an end of the third locus-specific hybridization probe hybridizes with a third base that has a distance of 0 to 1 Mbp proximal to the second chromosome segment, and an end of the fourth locus-specific hybridization probe that comes closest to the second chromosome segment hybridizes with a fourth base that has a distance of 0 to 1 Mbp distal from the second chromosome segment, and generates a fusion signal A-B in a signal pattern generated by in situ hybridization, and wherein the third locus-specific hybridization probe and/or the fourth locus-specific hybridization probe in the second probe pair is/are marked with a further detection label X$_1$, thereby flanking the second chromosome segment and generating fusion signals and mixed signals A-BX$_1$ and/or AX$_1$-B in a signal pattern generated by in situ hybridization; and wherein the hybridization probes are labeled directly with the detection labels.

5. The composition according to claim 1, wherein the first chromosome segment is a first breakpoint region and the second chromosome segment is a second breakpoint region.

6. The composition according to claim 1, wherein the detection labels are fluorescent labels.

7. The composition according to claim 6, wherein the detection labels A and B are selected from the group consisting of labels emitting in the emission regions green and orange/red.

8. The composition according to claim 1, wherein the composition comprises at least six different locus-specific hybridization probes, wherein said at least six locus-specific hybridization probes comprise said first probe pair, said second probe pair, and a third probe pair wherein said third probe pair is configured to hybridize with nucleic acid sequences flanking a third chromosome segment proximally and distally.

9. The composition according to claim 1, wherein at least two of the first, second, third, or fourth locus-specific hybridization probes are each marked with at least one further detection label that is different from the detection labels A, B, and X$_1$.

10. The composition according to claim 1, wherein the first chromosome segment and the second chromosome segment are each at least 500 bp.

* * * * *